US005232665A

United States Patent [19]

Burkovich et al.

[11] Patent Number: 5,232,665

[45] Date of Patent: Aug. 3, 1993

[54] MULTI-LINEAR AUTOMATIC APPARATUS FOR PROCESSING IMMUNOASSAYS

[75] Inventors: Robert A. Burkovich, Newark, Del.; James H. Lipscomb, Kennett Square, Pa.; Colin A. Nurse, Newark; Kin W. Wong, Claymont, both of Del.; Paul J. Zuk, Lincoln University, Pa.; Robert E. Bernstine, Chesapeake City, Md.

[73] Assignee: E. I. Du Pont de Nemours and Company, Wilmington, Del.

[21] Appl. No.: 736,157

[22] Filed: Jul. 26, 1991

[51] Int. Cl.[5] .................. G01N 33/00; C12M 1/00; C12M 1/40

[52] U.S. Cl. .................. 422/65; 422/63; 435/287; 435/288

[58] Field of Search .................. 422/63, 65; 435/287, 435/288

[56] References Cited

U.S. PATENT DOCUMENTS

| | | | |
|---|---|---|---|
| 4,066,412 | 1/1978 | Johnson et al. | 422/65 |
| 4,265,855 | 5/1981 | Mandle et al. | 422/65 |
| 4,297,337 | 10/1981 | Mansfield et al. | 424/1 |
| 4,315,891 | 2/1982 | Sakurada | 422/64 |
| 4,459,265 | 7/1984 | Berglund | 422/64 |
| 4,628,037 | 12/1986 | Chagnon et al. | 436/526 |
| 4,661,408 | 4/1987 | Lau et al. | 428/405 |
| 4,672,040 | 6/1987 | Josephson | 436/526 |
| 4,698,302 | 10/1987 | Whitehead et al. | 435/94 |
| 4,837,159 | 6/1989 | Yamada et al. | 436/45 |
| 4,861,554 | 8/1989 | Sakuma | 422/65 |
| 4,937,048 | 6/1990 | Sakai et al. | 422/63 |
| 5,104,808 | 4/1992 | Laska et al. | 436/48 |

FOREIGN PATENT DOCUMENTS

| | | |
|---|---|---|
| 0314525 | 5/1989 | European Pat. Off. . |
| 0356250 | 2/1990 | European Pat. Off. . |
| 2591344 | 6/1987 | France . |
| 2199407 | 7/1988 | United Kingdom . |
| 2239093 | 6/1991 | United Kingdom . |

OTHER PUBLICATIONS

Patent Abstracts of Japan, vol. 13, No. 87, p. 835, Abstract of JP 63-271164, Publ. 1988-11-09 (Shimadzu Corp.).

*Primary Examiner*—Robert J. Warden
*Assistant Examiner*—T. A. Trembley

[57] ABSTRACT

The apparatus processes immunoassays of samples using a solid support. It provides a compact system using rectilinear motion to process carriers holding samples on a real time basis while permitting the input and output of the system to operate on a random basis.

21 Claims, 17 Drawing Sheets

30
34
36
18
10
12
32
14
16
19

12
18
68
66
64
60
520
62
65
80
90
20
94
90
131
126
172
120

18'
18"
73
70
75
300
302
305
306
18
67
310
308
316
314
305
312
70
70
18'
302
75
69
306

258
102
286
288
100
90
59
94
134
133
96
110
132
120
122
124
127
128
126
131
130

422
408
420
410
418
421
400
416
404
414
90
424
412
120
12

572
12

550
504
514
570
508
506
502

270
262
268
272

258
286
102
288
288
100
90
94
101
92

WASH STATION
ROTARY VALVE
454
20
100
1
2
3
4
5
6
(#7)
8
9
10
32
168
26
452
WATER
450
PROBE WASH
466
RESUSPENSION BUFFER
464
WASH BUFFER
458
WASTE
460

START

INPUT TRAY AND PROCESSING CHAMBER HAS CARRIERS?
YES
NO
METHOD DECODE TASK
ENTRANCE AND EXIT STATIONS TASK
SIGNAL TASKS START
WASH STATIONS TASK
INCUBATION TASK
END
SLEEP FOR THE DURATION OF A FULL CYCLE
TRANSPORT TASK
YES
ALL TASK DONE ?
NO
DELAY FOR 1 SECOND;
SIGNAL CYCLE TIME ERROR.

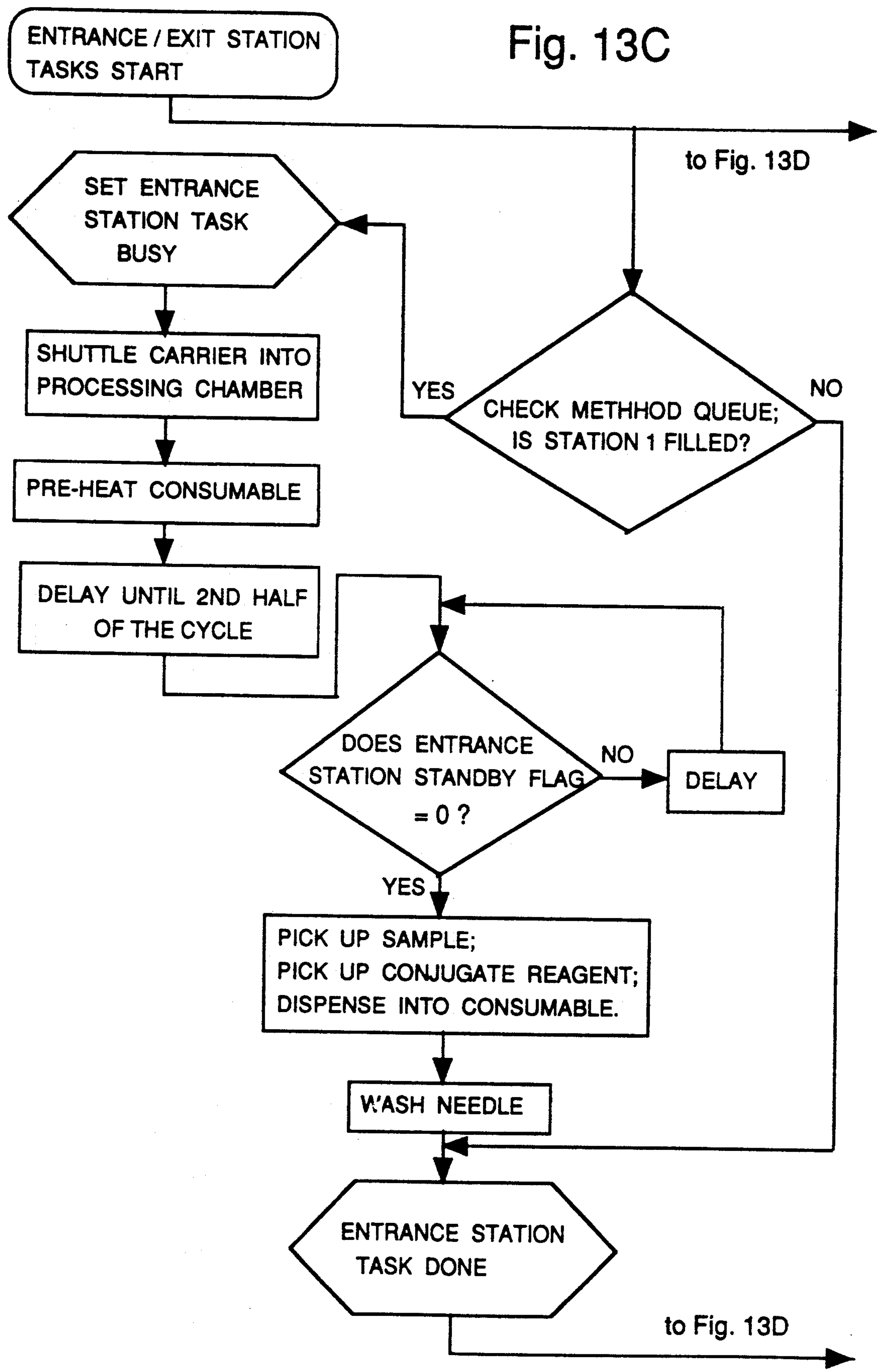
Fig. 13C
ENTRANCE / EXIT STATION TASKS START
to Fig. 13D
SET ENTRANCE STATION TASK BUSY
SHUTTLE CARRIER INTO PROCESSING CHAMBER
YES
CHECK METHHOD QUEUE; IS STATION 1 FILLED?
NO
PRE-HEAT CONSUMABLE
DELAY UNTIL 2ND HALF OF THE CYCLE
DOES ENTRANCE STATION STANDBY FLAG = 0 ?
NO
DELAY
YES
PICK UP SAMPLE;
PICK UP CONJUGATE REAGENT;
DISPENSE INTO CONSUMABLE.
WASH NEEDLE
ENTRANCE STATION TASK DONE
to Fig. 13D

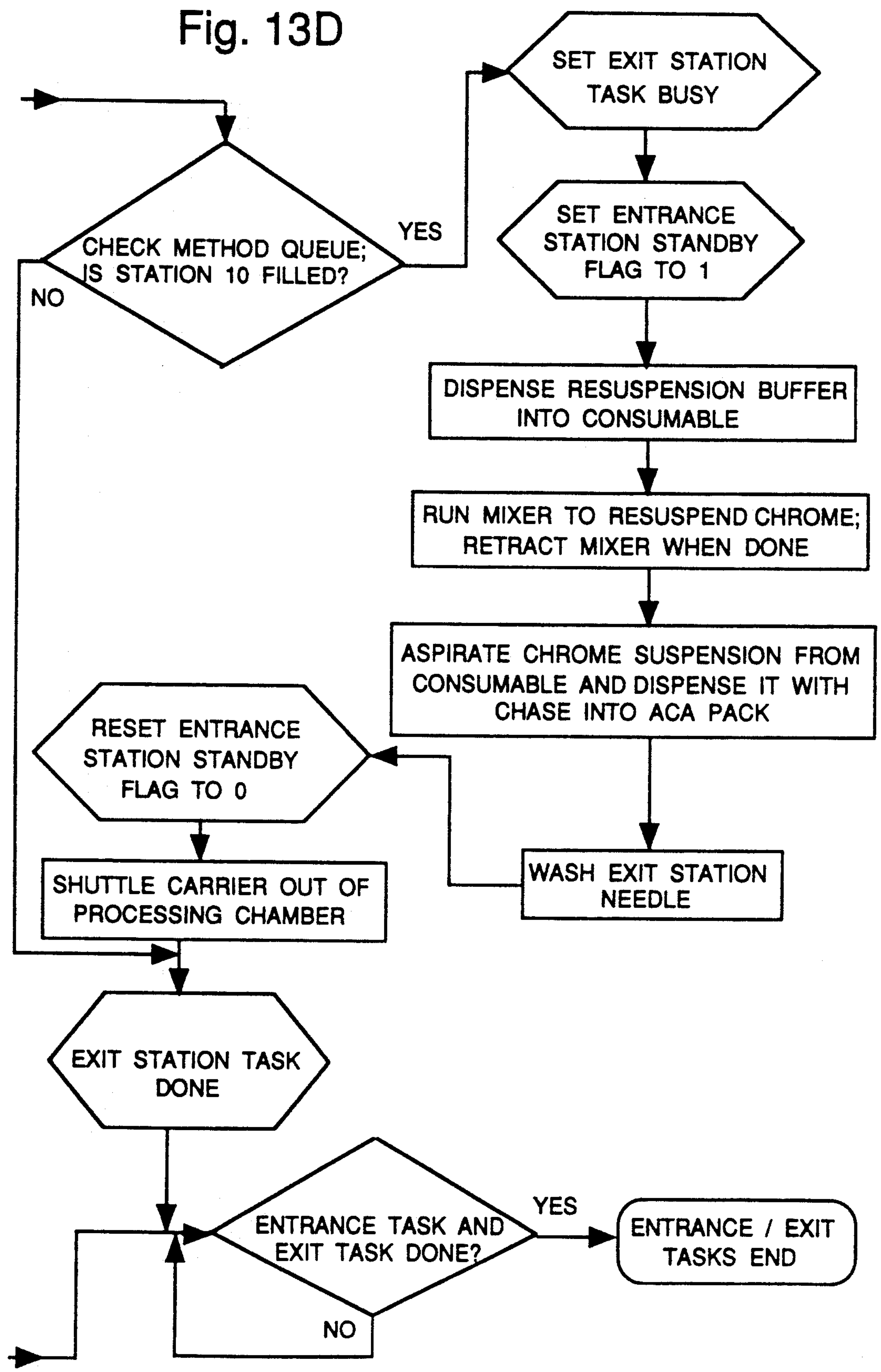
Fig. 13D
CHECK METHOD QUEUE; IS STATION 10 FILLED?
YES
NO
SET EXIT STATION TASK BUSY
SET ENTRANCE STATION STANDBY FLAG TO 1
DISPENSE RESUSPENSION BUFFER INTO CONSUMABLE
RUN MIXER TO RESUSPEND CHROME; RETRACT MIXER WHEN DONE
ASPIRATE CHROME SUSPENSION FROM CONSUMABLE AND DISPENSE IT WITH CHASE INTO ACA PACK
WASH EXIT STATION NEEDLE
RESET ENTRANCE STATION STANDBY FLAG TO 0
SHUTTLE CARRIER OUT OF PROCESSING CHAMBER
EXIT STATION TASK DONE
ENTRANCE TASK AND EXIT TASK DONE?
YES
NO
ENTRANCE / EXIT TASKS END

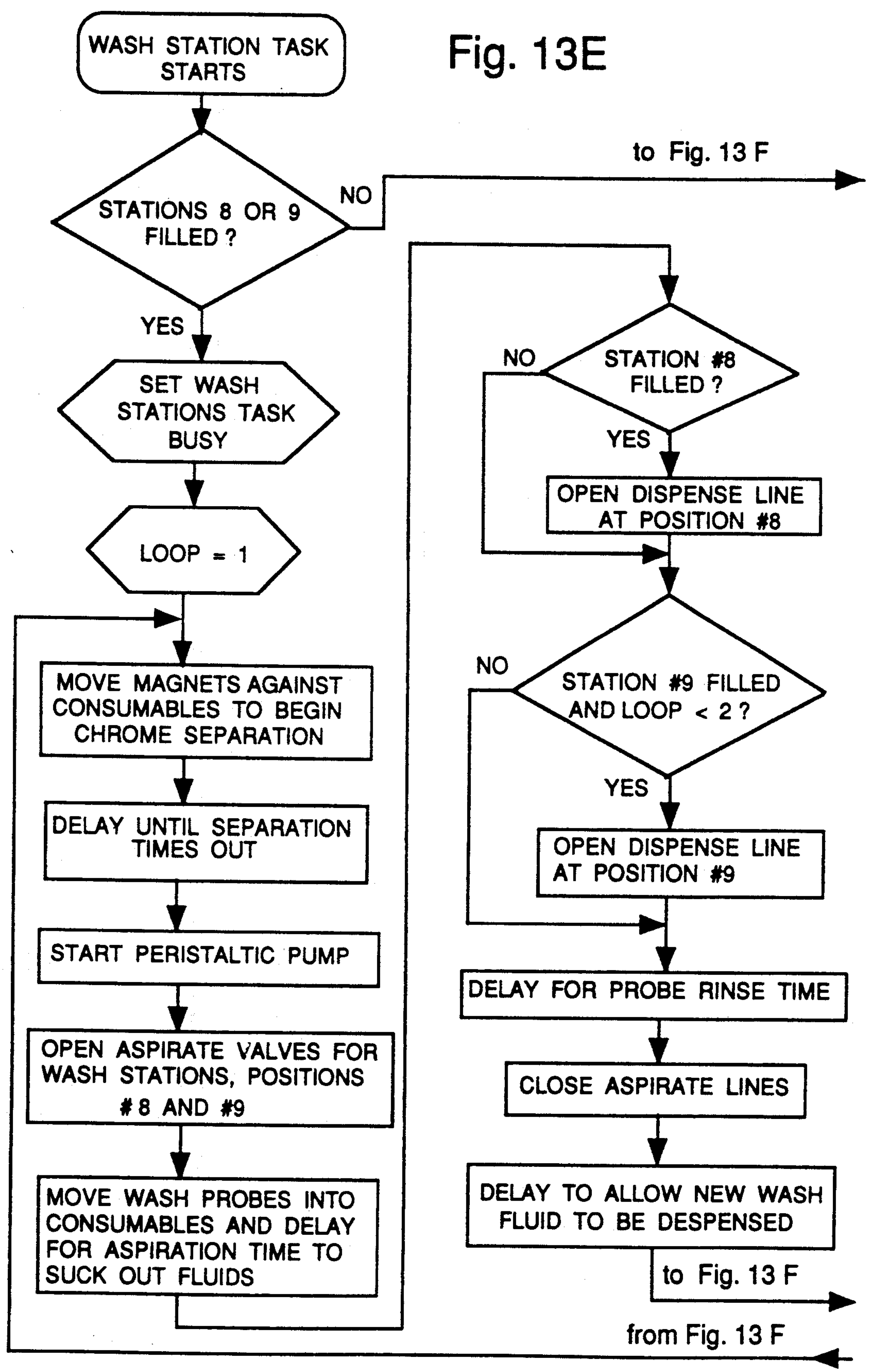
WASH STATION TASK STARTS
Fig. 13E
to Fig. 13 F
STATIONS 8 OR 9 FILLED ?
NO
YES
SET WASH STATIONS TASK BUSY
LOOP = 1
MOVE MAGNETS AGAINST CONSUMABLES TO BEGIN CHROME SEPARATION
DELAY UNTIL SEPARATION TIMES OUT
START PERISTALTIC PUMP
OPEN ASPIRATE VALVES FOR WASH STATIONS, POSITIONS #8 AND #9
MOVE WASH PROBES INTO CONSUMABLES AND DELAY FOR ASPIRATION TIME TO SUCK OUT FLUIDS
STATION #8 FILLED ?
NO
YES
OPEN DISPENSE LINE AT POSITION #8
STATION #9 FILLED AND LOOP < 2 ?
NO
YES
OPEN DISPENSE LINE AT POSITION #9
DELAY FOR PROBE RINSE TIME
CLOSE ASPIRATE LINES
DELAY TO ALLOW NEW WASH FLUID TO BE DESPENSED
to Fig. 13 F
from Fig. 13 F

MULTI-LINEAR AUTOMATIC APPARATUS FOR PROCESSING IMMUNOASSAYS

CROSS REFERENCE TO RELATED APPLICATIONS

Subject matter disclosed herein is disclosed or claimed in copending applications Method and Apparatus for Automatically Processing Magnetic Solid Phase Reagents, filed Aug. 10, 1988, Ser. No. 07/230,449, now U.S. Pat. No. 5,147,529 issued Sep. 15, 1992. Method and Apparatus for Effecting the Automatic Analytical Testing of Samples, filed Aug. 26 1988, Ser. No. 07/237,119, now U.S. Pat. No. 5,104,808 issued Apr. 14, 1992, Vortex Mixer Drive, filed Jul. 26, 1991, now U.S. Pat. No. 5,104,231 issued Apr. 14, 1992 and Carrier Device, filed Jul. 26, 1991, Ser. No. 07/736,155.

FIELD OF THE INVENTION

The present invention relates to an automated apparatus for analyzing liquid samples, and, more particularly, to apparatus for processing samples for quantitatively determining the presence of a variety of substances, including antibodies, antigens and various proteins, including cancer markers and hormones, in biological samples.

BACKGROUND OF THE INVENTION

Heterogeneous immunoassays typically are performed using a solid support, preferably with the solid support being formed from magnetic particles. A particularly preferred support for this purpose is that described in U.S. Pat. No. 4,661,408 assigned to E.I. du Pont de Nemours & Co., Inc. This patent describes a chromium dioxide particle which has favorable magnetic properties for use as a solid support in such assays.

The concept of using magnetically responsive particles to effect separations of bioactive materials is old in the art (Hedin, C.G., Biotech. Bioeng. Symp. No. 3 (1972) 173-174; Robinson, P.J., et al., Biotech Bioeng. (1973) 15, 603-606). The concept has been extended over time to include affinity purification of enzymes, proteins or microorganisms applicable to any sorption-desorption process (Dunhill, P., et al., Biotech. Bioeng. (1974) 10, 987-990; Horisberger, M., Biotech. Bioeng. (1976) 18, 1647-1651).

Another improved magnetically responsive particle is described by Mansfield et al. in U.S. Pat. No. 4,197,337. These particles are porous glass microparticles with magnetic material imbedded within them. This gives the particles the properties of high surface area, inertness and being substantially superparamagnetic. This high surface area again favors rapid reaction kinetics and increases capacity of the individual particles. Being substantially superparamagnetic, basically means the particles do not retain much magnetic memory, or retentivity, when removed from a magnetic field. This means that particles can be repeatedly separated from their environment by a magnetic field without affecting the ability to redisperse those particles. This is of advantage in sandwich immunoassays where multiple washing steps may require repeated separation and redispersion.

The protected $CrO_2$ particles described in the Du Pont patent have several properties that are particularly advantageous in heterogeneous immunoassays. These are:

low remanent magnetism and favorable surface structure—allowing repeated magnetic separation/dispersion cycles; rapid separation in a magnetic field; high surface area for high capture capacity; a highly stable particle for maximum reagent shelf life.

One problem with immunoassays is that they require repeated washing of the solid support containing the bound component following removal of the free component. This is a particularly difficult procedure even when performed manually. It is a particular problem when the automatic wash procedure is incorporated into an automatic instrument which is capable of performing immunoassays. The typical requirements for purity in such immunoassays is that the bound component remaining following such washes should not contain more than 20 parts per million of the original sample/conjugate matrix. This necessitates the use of multiple wash stations and can be accomplished in automatic instruments by providing such multiple wash stations. However, the several mechanisms required to operate individually the several wash stations and the mechanisms required for the wash stations themselves can become quite expensive.

There are essentially two types of heterogeneous immunoassays. These are competitive immunoassays and sandwich immunoassays. In a competitive assay, an antibody to an antigen contained in a first reagent is attached to the derivatized magnetic particles to make up a solid phase. The second reagent, consisting of antigen attached to a tag (a measurable entity, including radioactive molecules, fluorescent molecules, or enzymes), and patient sample are mixed with the solid phase in a test tube. In the absence of patient antigen, some 50% of the antigen-tag is bound to the antibody of the magnetic solid phase. In the presence of patient antigen, some of the antibodies are filled up with patient antigen and are unavailable to the tag antigen. As a result, increasing amount of patient antigen leads to decreasing amount of tag antigen. Thus one can form a calibration chart relating the amount of patient antigen to the amount of tag antigen. The separation and wash stages results from the need to measure the free tag or the bound tag, not the total tag added. The magnetic particle facilitates this separation by forming the particles with the bound tag into a pellet on the side of the tube. The free tag can then be removed as by aspiration. Following the separation and removal of free tag, another reagent is added so that the amount of bound tag can be measured. In a typical case, enzyme is used as the tag so that the reagent added is a substrate for the enzyme permitting the measurement of the amount of tag that was bound to antibody.

In a typical sandwich immunoassay, an antibody to an antigen is attached to the magnetic particle. This is in high concentration relative to the amount of patient antigen in a sample. Patient antigen is captured by the antibody on the magnetic particles and then the particles (and captured patient antigen) separated from interfering substances in the sample. To this, a second reagent, containing a second antibody with an attached tag, is added. This second antibody attaches to the patient antigen, captured by the first antibody on the magnetic particle, and results in the formation of a sandwich so that the second antibody tag is held firmly by the antigen to the first antibody on the magnetic particle. At this point, a magnetic separation similar to that described, permits the determination of bound tag which is in proportion to the patient antigen, the excess tag of the second reagent having been removed by aspiration.

Magnetic particles are particularly useful as the solid support in heterogeneous immunoassay because they can readily separate the free from the bound tag. Such immunoassays using magnetic particles as a solid support are described for example in U.S. Pat. No. 4,661,408 (Lau et al.), U.S. Pat. No. 4,628,037 issued to Chagnon et al., U.S. Pat. No. 4,672,040 issued to Josephson, and U.S. Pat. No. 4,698,302 issued to Whitehead et al. The methods disclosed in all of these patents separation units such as those that are available from Corning Medical, Corning Glass Works, Medfield, Mass. Such manual techniques are relatively slow, require relatively strong magnets which are expensive, require considerable manual dexterity, and require an excessive amount of time to effect the separation with the purity required, particularly for sandwich type heterogeneous immunoassays.

There are numerous automatic clinical analysis type instruments available on the market today. Typical of these is the Automatic Clinical Analyzer known as the aca® sold by E.I. du Pont de Nemours & Co., Inc. of Wilmington, Del. This is an instrument in which an incubator is used to process samples. The incubator is in the form of a belt or chain in which a sample mixed with reagents in packs and is analyzed for its various components. While quite satisfactory for many purposes it does not have the versatility required for some of the more recently developed sensitive immunoassays.

Other analyzers that are available for analyzing samples are those that are described, for example, in U.S. Pat. No. 4,315,891 assigned to Olympus Optical Company. This patent describes a belt or chain incubator and has a single reaction line in which reaction vessels are carried step by step along the reaction line. Samples and reagents are delivered to the vessels during their movement along the reaction line to obtain a test liquid which is then subjected to photometric analysis. This machine permits several tests to be run simultaneously on samples by an interleaving processing. Unfortunately, this apparatus does not have the capability for performing the precise washing required in heterogeneous immunoassays. The apparatus also requires a relatively large amount of space.

Another automatic analytical apparatus is that described in U.S. Pat. No. 4,459,265 assigned to Clinicon. This apparatus includes a stepwise rotatable circular plate. It carries a plurality of reaction tubes on its periphery with several reagent supply stations arranged at different locations around such periphery. The use of multiple stations does provide the machine with the versatility to carry out several different test methodologies, but again does not provide the necessary washing required for the more sensitive heterogeneous immunoassays.

Many of the machines described use circular trays that rotate to provide the necessary random access to add sample and reagent to, incubate, wash the magnetic particles, etc., in the reaction vessels. This creates the need for greater space requiring larger instruments that would otherwise be desirable. It is also necessary in such instruments to have random access of the samples to be processed to the real time of the immunoassay system.

SUMMARY OF THE INVENTION

Many of these problems of the prior art apparatus for performing immunoassays, including those which use magnetic particles, i.e., particles that are responsive to a magnetic field, are reduced using the apparatus of this invention. The apparatus permits immunoassays to be processed, using such magnetic particles, and yet is compact.

This invention provides an automatic multilinear apparatus for processing immunoassays of samples using a solid support, the assays having bound and free phases, the bound phase being bound to the solid support, the apparatus comprising: an inlet chamber, a plurality of carriers positioned in the inlet chamber, each carrier holding a sample, a rotatably mounted reaction vessel, particles responsive to a magnetic field, reagents, and a reaction product container, a processing chamber generally parallel to the inlet chamber, first means to transport the carriers linearly in a first direction to one end of the inlet chamber, second means to transport sequentially the carriers linearly in a second direction transverse to the first direction from the one end of the inlet chamber to one end of the processing chamber, first translating means for acting on each carrier at the one end of the processing chamber to transfer each carrier's sample and reagents into the carrier's reaction vessel, third means to transport sequentially the carriers linearly in a third direction opposite to and generally parallel to the first direction to several processing positions, means for vortexing at at least one processing position by nutating the lower portion of each carrier reaction vessel, wash means at at least one processing position for removing liquids from each carrier's reaction vessel and replacing the liquids with a different liquid, magnet means at each wash means position for applying a magnetic field to each carrier reaction vessel prior to liquid removal, second translating means at the last sequential processing position for transferring the contents of each carrier's reaction vessel to its container, fourth means to transport each carrier transversely of the third direction from the processing chamber to the other end of the inlet chamber, and fifth means to transport each carrier from the other end of the inlet chamber in a direction generally parallel to the first direction for storage.

In a preferred embodiment of the invention, each carrier is provided with at least a pair of receptacles positioned at the bottom of the carrier, and the second means has a pair of spring loaded pins foldable downwardly in the second direction, whereby the second means can be displaced in a direction opposite the second direction to engage each pair of receptacles and transport each carrier in the second direction.

In another embodiment of the invention, the third means includes pairs of pins fixed adapted to engage each of the plural carrier receptacles and rectilinear transport means for raising each of the pair of fixed pins to engage the receptacles and displace the carrier's one processing position, and lowering each of the pairs of fixed pins to disengage the receptacles.

In still another embodiment of this invention the magnet means includes a magnet, and means to displace the magnet to engage the side of a reaction vessel, thereby to apply the magnetic field to the particles.

This apparatus permits the apparatus to be used for heterogeneous immunoassays and require only a limited amount of space and yet permits random access to a real time immunoassay process.

BRIEF DESCRIPTION OF THE DRAWINGS

The invention will be better understood with reference to the several drawings in which like reference numerals are used to indicate like components, in which.

DETAILED DESCRIPTION OF THE PREFERRED EMBODIMENT

Figure 1:
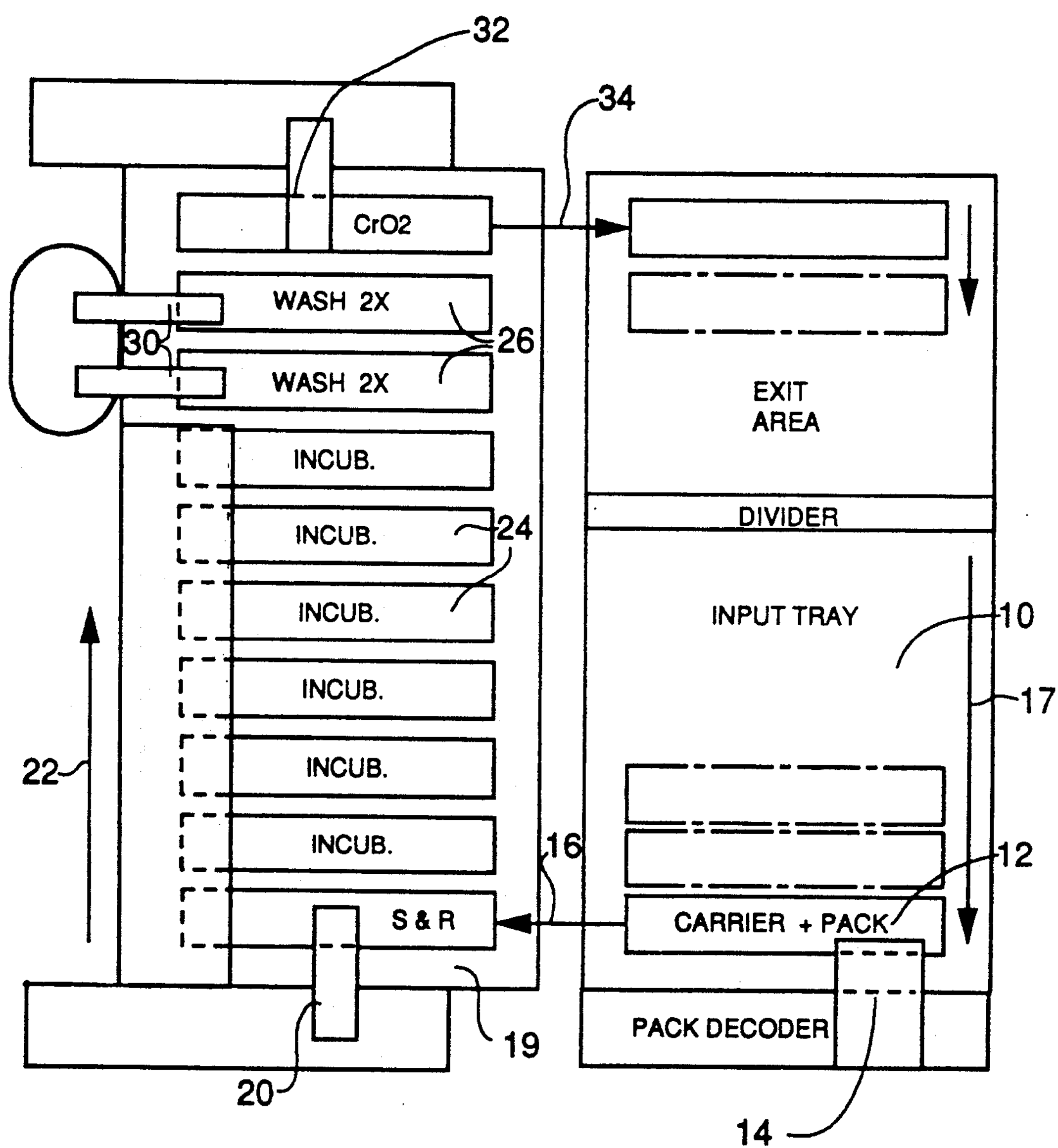
FIG. 1 is block diagram of an automatic multilinear apparatus for processing immunoassays of samples using magnetic particles as solid support in accordance with this invention.

As may be seen in FIG. 1, there is a block diagram illustrating an analyzer in which the apparatus of this invention. The analyzer has an input or inlet chamber 10 in which there are held a plurality of carriers 12. Each carrier 12 holds a sample holder for a sample to be processed, a flexibly mounted reaction vessel 100. There are magnetic particles 101 (FIG. 11) in the reaction vessel 100, i.e., particles that are responsive to a magnetic field, along with reagents for performing immunoassays. The carrier 12 also holds a transparent removable container or pack 272 that is introducible into another instrument for evaluating the processed immunoassay reaction. An optical decoder 14 is positioned at the lower portion of the inlet chamber (in the drawing) for decoding a code on the sample holder in the carrier 12 which will identify the particular test to be run so that the analyzer may be actuated properly.

A first transport 17 moves the carrier 12 linearly in a first direction and urges the carriers 12 against the decoder 14. Once decoded, a shuttle mechanism 16 transports the carriers 12 linearly in a second direction transverse to the first direction from one end of the inlet chamber 10 to one end of a processing chamber 19. The processing chamber 19 is generally parallel to the inlet chamber 10 and is so positioned to minimize the space occupied by the entire processing unit. A first translator symbolized by the block 20 acts on each carrier 12 to transfer each carrier's sample and reagents into the carrier's reaction vessel 100. A transport mechanism 22 sequentially transports the carriers 12 linearly in a third direction opposite to and generally parallel to the first direction to several processing positions 24. At the second, fourth and sixth processing positions 24 are means of vortexing each carrier's reaction vessel 100. At the eighth and ninth processing positions, wash means 26 are provided for removing liquids from each carrier reaction vessel 100 and replacing the liquids with a different liquid. Translating means 30 are provided at each wash position to apply a magnetic field to each carrier reaction vessel 100 prior to removal of the liquid so as to position the magnetic particles against walls of the reaction vessel.

Finally, a second translating means 32 at the last processing position transfers the contents of each carrier's reaction vessel 100 into its container 272 for storage until analyzed. A fourth transport means 34 transports each carrier 12 transversely of the third direction from the processing chamber back into the other end of the inlet chamber. Finally, a fifth means 36 operates to transport each carrier 12 from the other end of the inlet chamber 10 in a direction generally parallel to the first direction for storage. Following storage, the carriers 12 may be removed at will so that the container 272 can be removed therefrom and put into a suitable analyzer for analysis such as the aca® Clinical Analyzer sold by E.I. du Pont de Nemours and Company, Wilmington, Del.

The multilinear apparatus provided thus is seen to provide a significant space saving and yet permits the apparatus to operate randomly against the real time requirements of a processing system for analyzing samples, i.e., it permits randomly entering samples into and removing samples from the system as desired.

Figure 2:
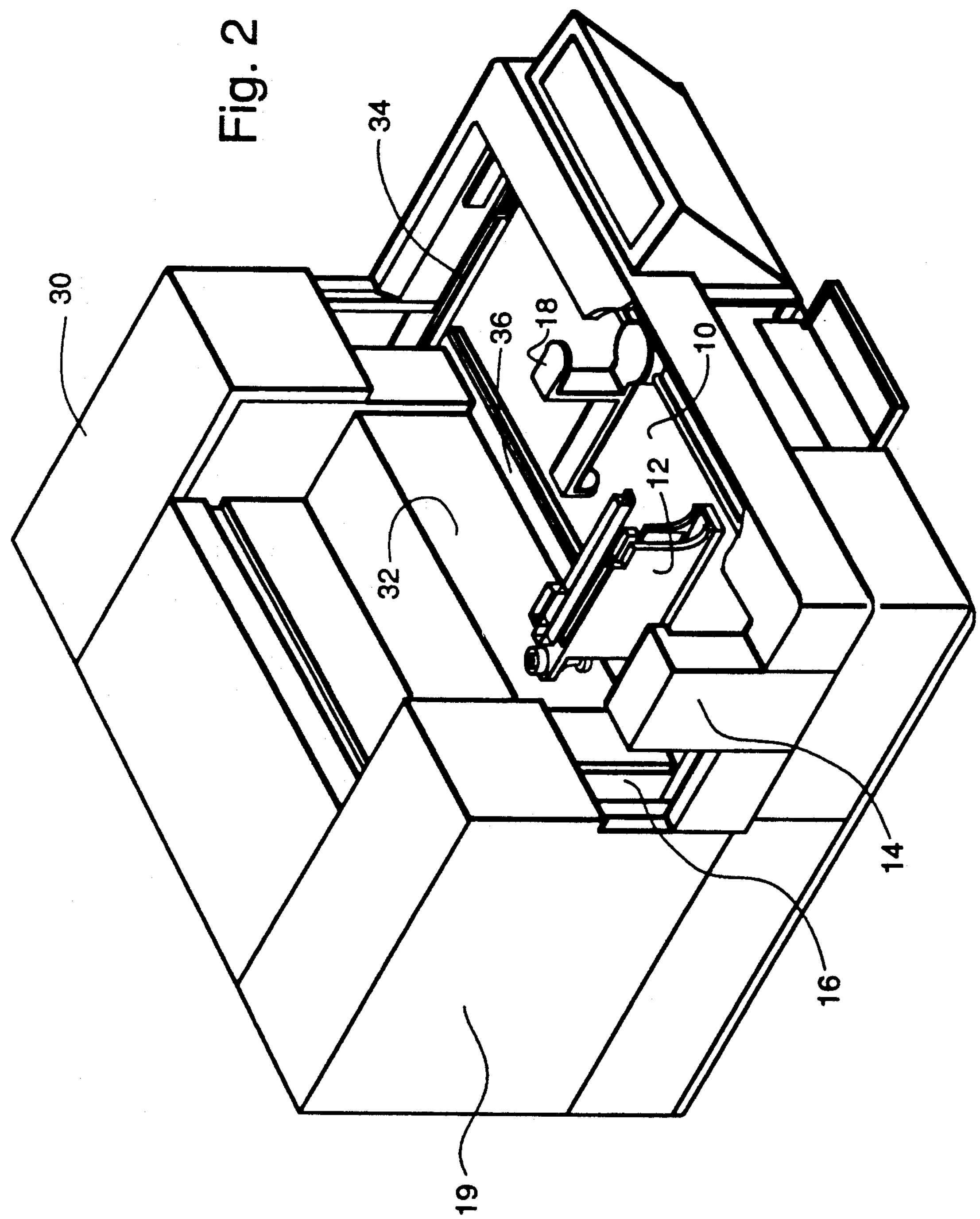
FIG. 2 is a pictorial view of the automatic multilinear apparatus of FIG. 1 constructed in accordance with this invention.

There may be seen in FIG. 2 a pictorial view of the instrument depicted functionally in FIG. 1. Thus in FIG. 2 there is an inlet chamber 10, carrier 12, first transport mechanism 16, optical decoder 14, processing chamber 19, and rectangular motion transport mechanism 32. The unit also includes, typically in the box portion 500 (FIG. 3), the electronics and software that control the operation of the system as will be described hereinafter.

In FIGS. 3 to 12 more detail of the system depicted in FIGS. 1 and 2 is shown. Thus in these figures there may be seen the first transport means or carrier drive 17 connected to be driven by a spring loaded belt 152 which is actuated by a motor 154. The carrier drive 17 is guided in its operation by guide bars 156. The first transport mechanism 16 (FIG. 4) comprises a pair of pins 60 which are spring loaded so as to be foldable in a first direction, i.e., the direction necessary to move the carriers 12 from the inlet chamber 10 to the processing chamber 19. The pins 60 themselves are mounted on a bracket 62 which is mounted to be supported by bars 65 and a drive belt 66 which provides force for movement. The drive belt 66 is driven by a motor 68.

In their operation, the pins 60 of the first transport mechanism 16 are allowed to move to the right in the drawing, against the first direction, until the pins 60 engage receptacles 520 (FIG. 4) formed in the bottom of each carrier 12. Thus engaged, when the movement of the transport mechanism 16 is reversed to move in the first direction, the engaged carrier 12 is moved to the left in the drawing in the first direction into the processing chamber 19.

The processing chamber 19 includes a platform 67 having a plurality of pins 18 positioned thereon located at the spacing of each of several processing positions. In this illustration, the processing positions total 10 during which the reagents and sample in the reaction vessel 100 will be incubated, be washed and then moved out for further processing. The platform 67 is moved in a rectilinear motion so as to move forward in the direction depicted by the arrows 70 from one processing position to the next at intervals. Following each position movement, the platform 67 is lowered as indicated by the arrow 73 and dotted pins 18" (FIG. 5) so as to disengage from the several carriers. It is then moved backward against the arrow 70 (FIG. 3) to the next preceding processing position and then again raised as shown by arrow 69 and dotted pins 18" (FIG. 5) to engage the receptacles 520 in the carriers 12 at each preceding processing position. In this manner the carriers 12 are moved incrementally from one processing position to the next, to the next and so on. As the carriers 12 move to each processing position since the reaction vessel 100 in each case contains magnetic particles 101 (FIG. 11) which tend to settle they must be occasionally vortexed to resuspend the particles. This is accomplished by the mixer at processing position 2, 4, 6, 8, 9, and 10 depicted in FIG. 6. The carrier 12 for holding the reaction vessel is best seen in FIGS. 9–11.

Figure 9:
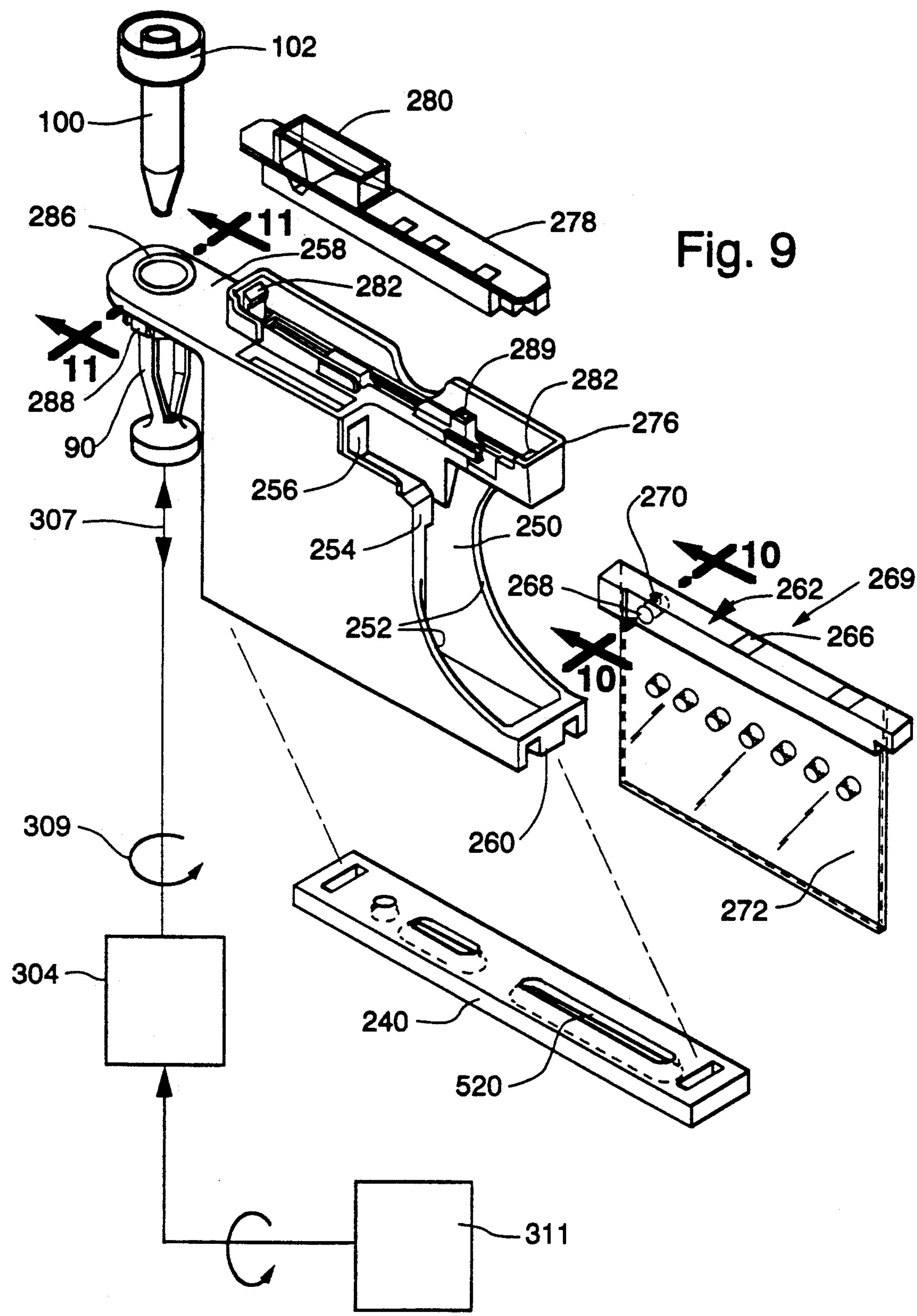
FIG. 9 is exploded view showing the features of the carriers used in this invention.
Figure 10:
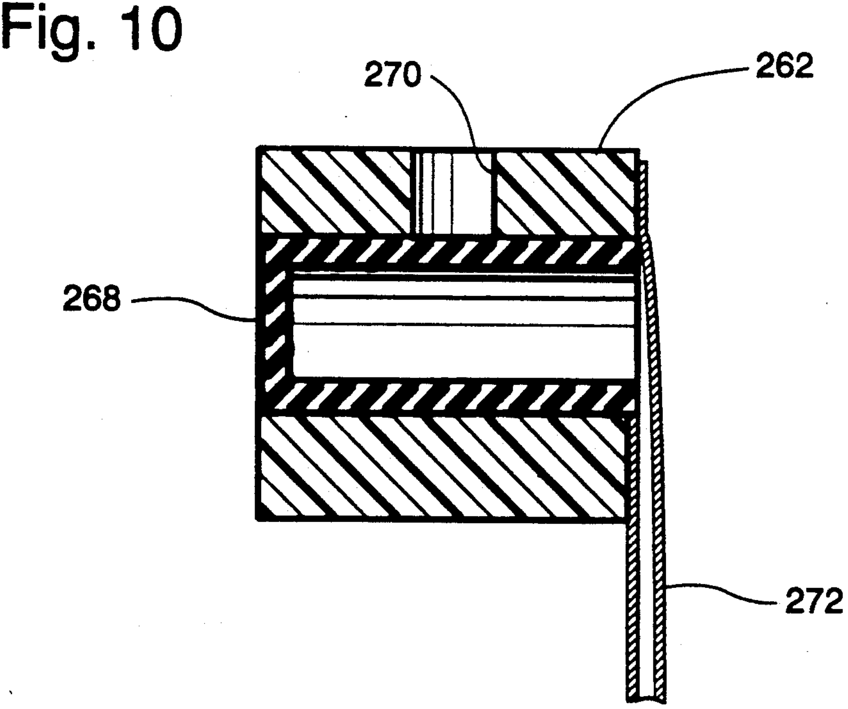
FIG. 10 is a sectional view taken along the section line 10—10 of FIG. 9.
Figure 11:
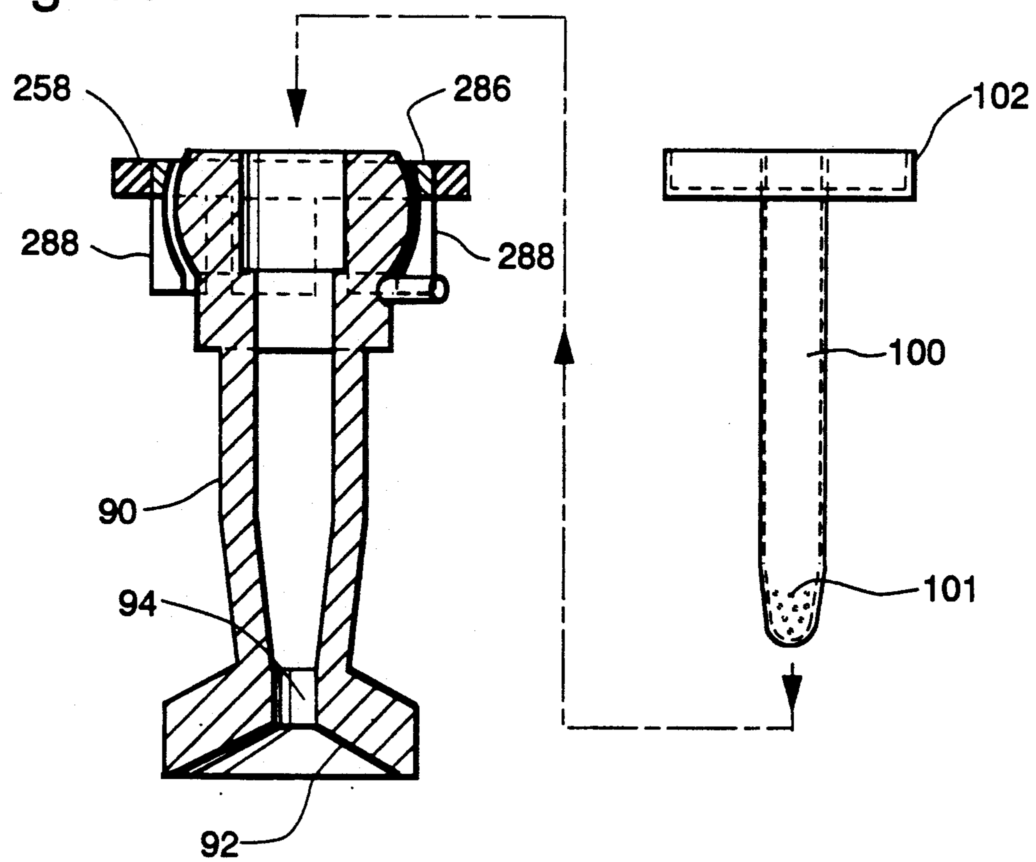
FIG. 11 is a sectional view taken along the section line 11—11 of FIG. 9.

There may be seen in FIGS. 9, 10 and 11 an exploded sectional view of one of the carriers 12 of FIG. 1. The carrier 12 is seen to contain a hollow, molded housing 250 defined by a pair of sidewalls 252, a top plate 258, and a base support 260. A drive bar 240 is positioned in the lower portion between the sidewalls 252 and is secured to the base support as by gluing. This drive bar 240 has receptacles 520 to facilitate its receiving drive pins for positioning the drive bar 240 and hence the carrier 12. The housing 250 may be formed of polysulfone or any other suitable engineering plastic which is rigid, strong and chemically inert. Attached to the front sidewall 252 (in the drawing) is a partition 254 which cooperates with the top plate 258 to accommodate the top frame of an analytical pack 262 which may be the same and preferably is the same as the aca® pack used in the aca® Automatic Clinical Analyzer sold by E.I. du Pont de Nemours and Company, Wilmington, Del. U.S.A. The aca® pack has identifying indicia 266 on the top which may be read by appropriate sensors to indicate the particular test being run and includes a septum 268 with an orifice 270 which may be used to introduce materials into a plastic pack 272. Since the aca® pack is well known it will not be described further.

In any event, the partition 254 and top plate 258 cooperate to define an orifice 256 adapted to accommodate the top member of the aca® pack 262 so it may be inserted into the carrier 12 with the lower side pack 272, which is formed of plastic material. The side pack is to slide in between the two side walls 252. The top of the carrier 12 also includes an elongated cup-like member 276 which is adapted to receive a removable sample reservoir 278 containing a reservoir 280. The sample reservoir 278 is held in the position within the opening 276 by appropriate molded grips 282. A fitting feature 289 to control access to the opening 276 may be provided for the sample reservoir 278.

To complete the carrier 12, the end of the top plate 258 may have an orifice 286 with downwardly extending flanges 288 adapted to hold a reaction vessel holder 90. The flanges 288 are concave on the inside to define a socket which cooperates with the bulbous top on a reaction vessel 90 in a ball and socket joint manner. The lower portion of the reaction vessel holder 90 may be shaped as depicted in FIG. 6 to have an inverted cavity or receptacle 92 (FIG. 11) at the upper end of which is hole 94 adapted to receive a pin 96 from a drive member, as will be described.

In an alternative embodiment of this invention, the reaction vessel holder 90 may be the reaction vessel itself although the use of the reaction holder vessel 90 is preferred for its long term stability and reliability. If the reaction vessel 90 as a tube holder is adapted to receive a reaction vessel 100, the reaction vessel 100 has at the upper portion thereof a concentric chamber 102 for holding reaction reagents that typically may be used, for example, in an immunoassay process.

Figure 6:
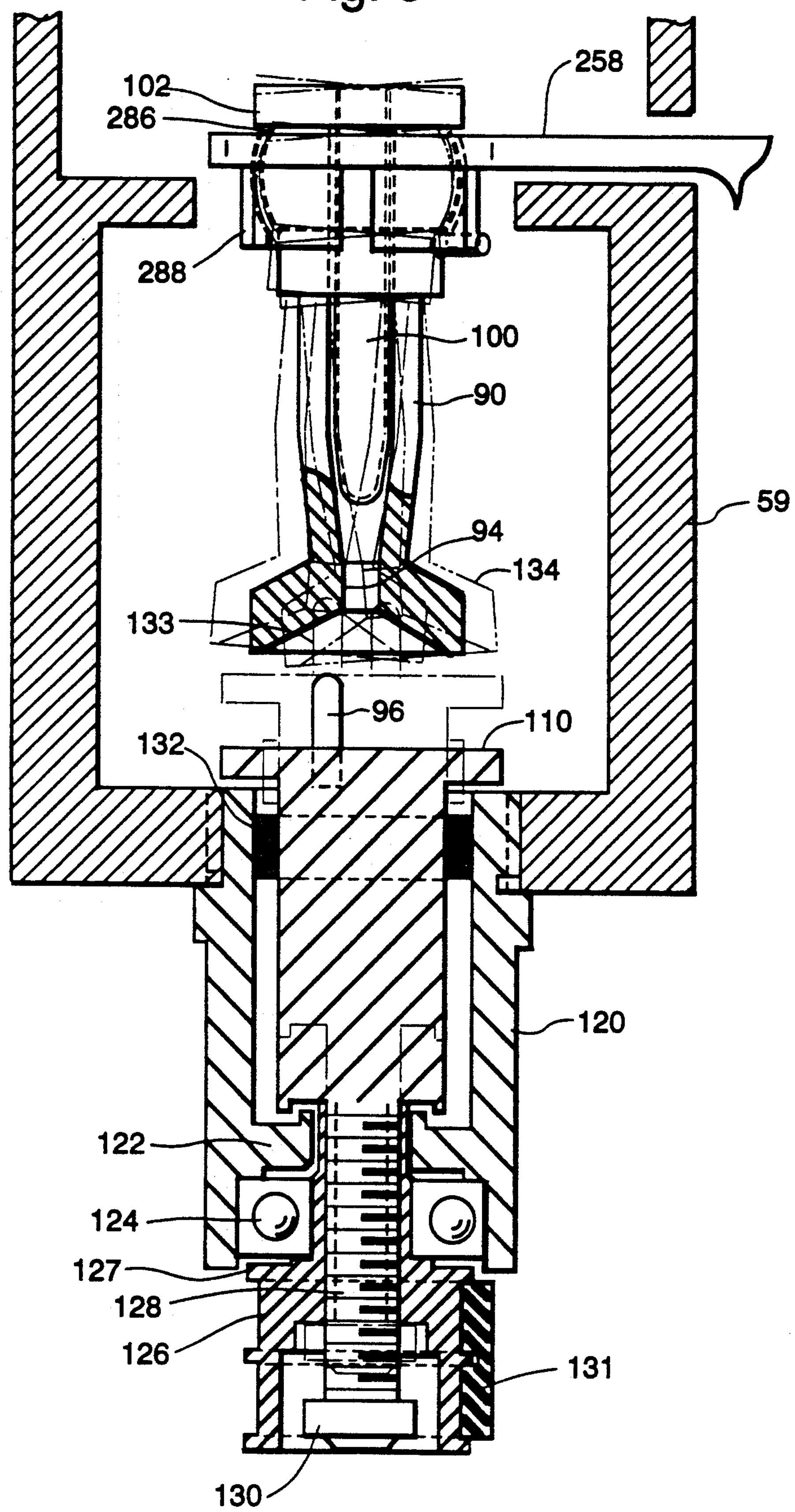
FIG. 6 is a view taken along the section line 6—6 of FIG. 3 to depict the mixer that is used to vortex the reaction vessels of this invention.
Figure 7:
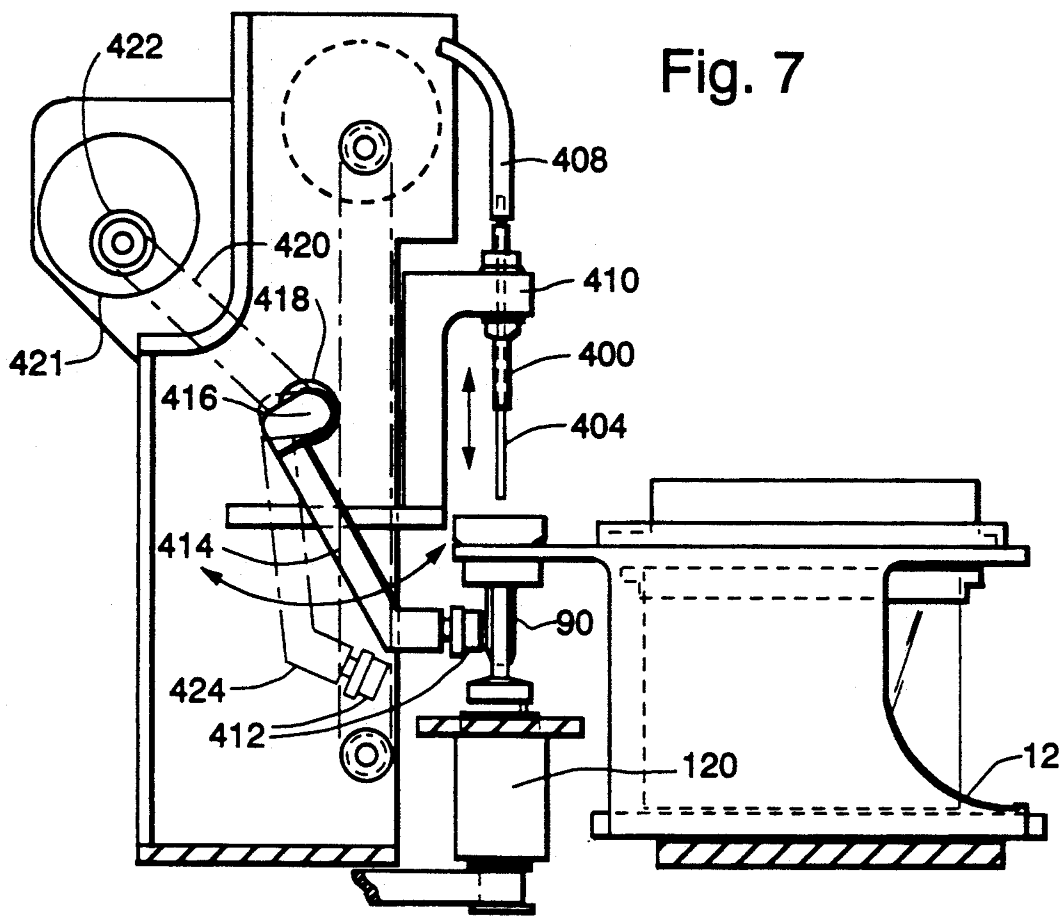
FIG. 7 is a view taken along the section line 7—7 of FIG. 3 to depict a wash station of this invention.

The reaction vessel holder 90 may be positioned in a thermal chamber 59 and is driven or nutated by the drive apparatus 304 and constructed in accordance with this invention and shown in detail in the cross sectional view of FIG. 6. This drive apparatus 304 mounted to the bottom of the thermal chamber 59 and provides a bidirectional motion as depicted by the line 307 (FIG. 9) as well as rotational motion as depicted by the line 309 to the reaction vessel holder 90. This drive apparatus 304 is powered by a single bidirectional drive motor 311 (FIG. 9) which provides rotational motion to the drive apparatus 304 (FIG. 9). The drive apparatus 304 engages the reaction vessel holder 90 by elevating a mixing cylinder or plate 110 on which the pin 96 is positioned contiguous the periphery at a point off of the elongated axis of the mixing cylinder 110. In other words the pin 96 engages the bottom end of the mixing vessel holder 90 into a position which is eccentric to the axis which mounts the mixing cylinder 110. The drive apparatus 304 then spins the mixing cylinder 110 moving the engaged end of the reaction vessel 100 to an orbit. If the reaction vessel 100 is managed so that it is free in two rotational directions of freedom, then the contents of the reaction vessel holder 90 will swirl or nutate thus mixing them. Reversal of the drive which spins the mixing cylinder 110 stops the orbiting of the reaction vessel 110 and lowers the mixing cylinder 110 thus disengaging the pin 96 from the reaction vessel holder 90.

The drive apparatus 304 (FIG. 9) has a cylindrical housing or base 120 which has an internal flange 122 for mounting a bearing 124 which in turn mounts a nut 127. The lower end (in the drawing) of the nut 127 is shaped to be cylindrical and hollow to accommodate a screw 128 which is threaded through the nut 127. At the top end of the screw 128 is formed an elongated cylindrical shaped mixer which defines a mixing cylinder 110 which as described mounts the eccentrically located pin 96. The lower end of the screw 128 has a locknut or disk 130 engaged thereon to limit the upper travel of the screw 128 in the nut 1276.

Figure 3:
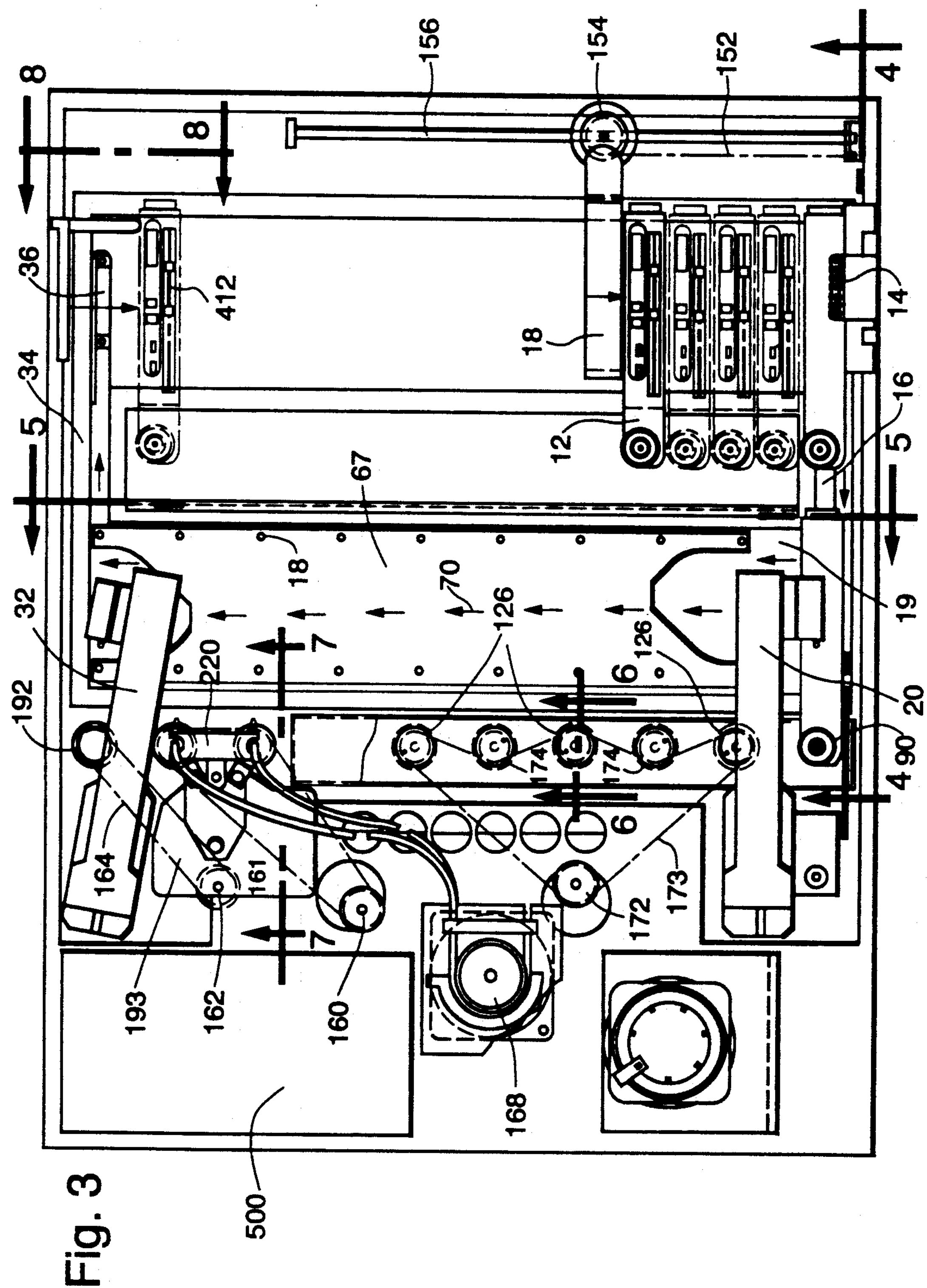
FIG. 3 is a plan view of the apparatus depicted in FIG. 2, partially broken away, to reveal the inner portion of the apparatus.
Figure 4:
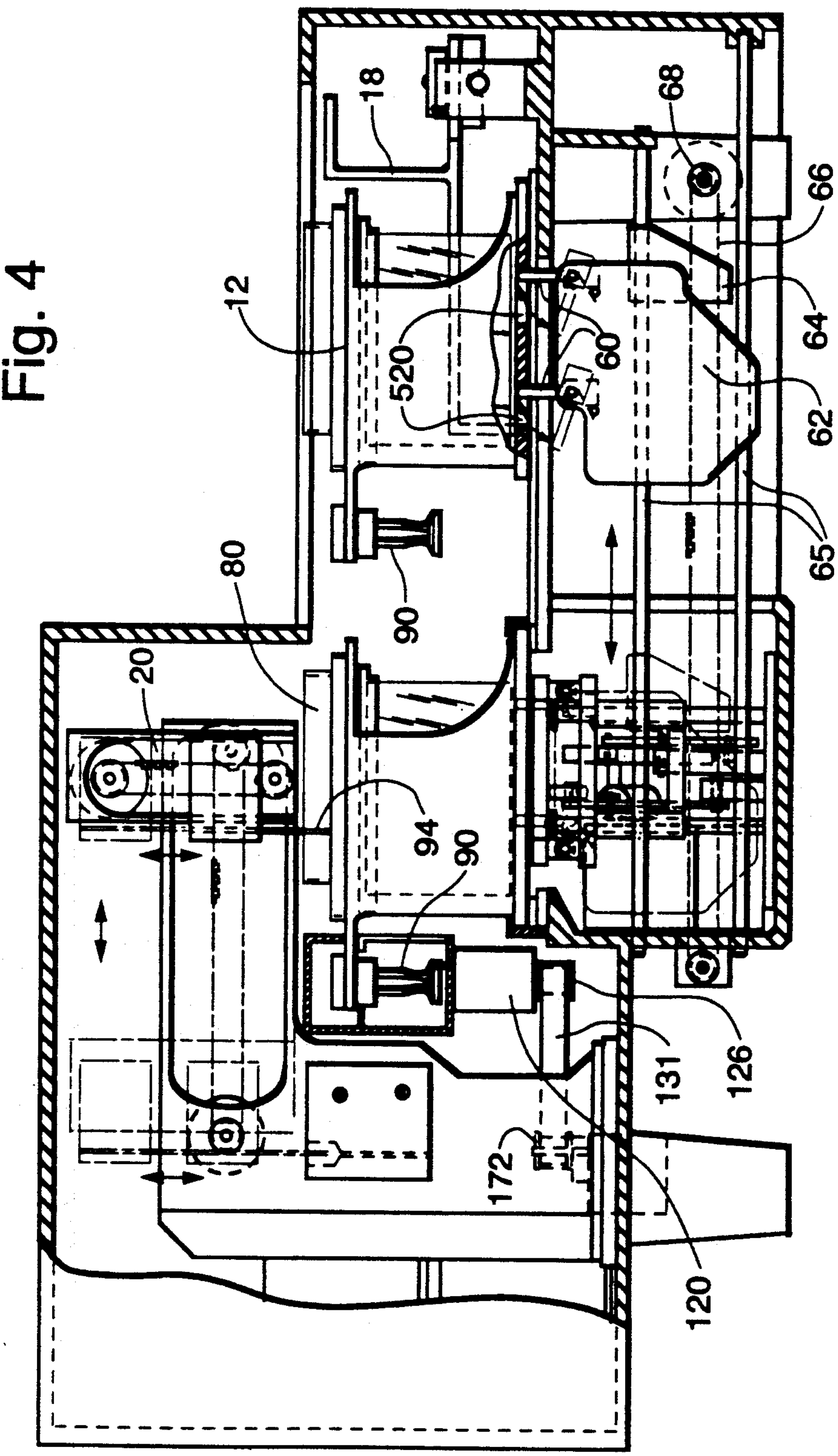
FIG. 4 is a section line taken along the 4—4 of FIG. 3 to illustrate a side elevational view of the apparatus of this invention.

Rotation of the mixing cylinder 110 is prevented by a leaf spring type clamp 132, only a portion of which is shown, which engages the periphery of the mixing cylinder 110 to inhibit its motion up to a degree. The leaf spring 132 is mounted to the base 120. The lower portion of the nut 127 is shaped to have the form of a drive pulley 126 to accommodate a drive belt 131 (FIG. 6) from a motor 172 (FIGS 3 & 4).

This automatic apparatus functions by rotating the nut 127 with a drive belt 131 attached to the pulley 126. The leaf spring 132 mounted on the base 120 drags on the outside diameter of the cylindrical mixing cylinder 110 and thereby acts as a rotational clutch to the screw 128 and mixing cylinder 110. When the nut 127 is thus rotated, the clutch prevents the screw 128 from rotating so instead the screw 128 elevates the mixing cylinder 110. This elevation continues until further elevation is prevented by the disk 130 at the bottom of the screw 128. At this point the clutch then slips allowing the nut 127, screw 128, mixing cylinder 110 and disk 130 to rotate together. By this time, the pin 96 has risen (dashed line 133) to engage the recess and ultimately the bore 94 in the mixing vessel holder 90.

The engagement is complete when the screw 128 reaches the top of the travel and thereafter the eccentric motion of the pin 96 causes the bottom of the reaction vessel holder 90 to rotate as depicted by the dashed line 134 and thereby causing vortexing to occur in the reaction vessel 100. If the rotation of the nut 127 is reversed the sequence starts over but in the opposite direction, i.e., the screw 128 is lowered until it strikes the flange 122. This invention is seen to be very advantageous. It functions with a small number of inexpensive parts. One drive motor permits the lifting and spin of the mixing cylinder 110. The device lends itself to be used with any number of duplicate devices and all to be driven by the same drive. It engages the bottom of the reaction vessel holder 90 or reaction vessel 100 gently so as to avoid on spilling of the vessel contents. Furthermore the engagement of the pin 96 in the hole or bore 94 is a very positive, reliable drive even if one of the vessels is mispositioned.

Figure 5:
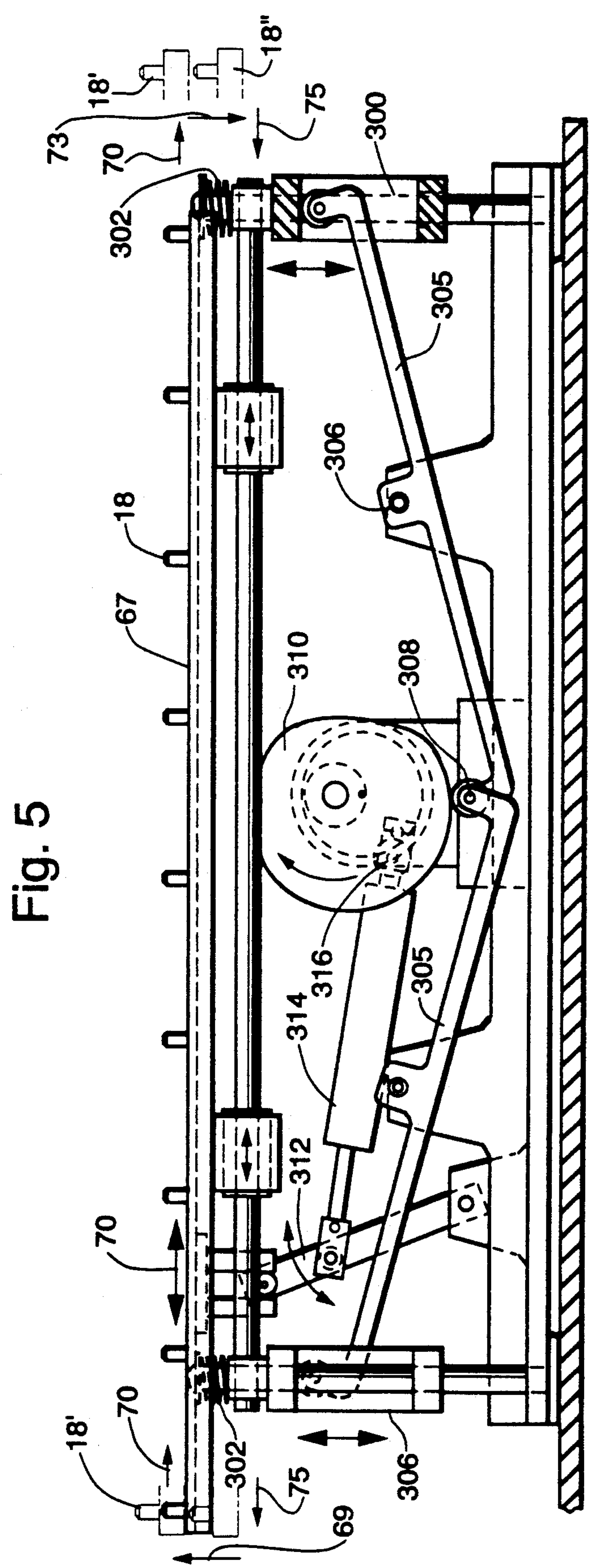
FIG. 5 is a sectional view taken along the section line 5—5 of FIG. 3 to depict the rectilinear, position by position advance mechanism for the carriers of this invention.

The details of the rectilinear, incremental advance mechanism are depicted particularly in FIG. 5. Thus in FIG. 5 may be seen the platform 67 mounted at either end by linear slides 300. The linear slides are spring loaded by springs 302 to elevate the platform 67. The linear slides 300 are driven by lever arms 305 which are pivoted at center pivot 306 and linked together at the common point 308 which is adapted to act as a cam follower to be driven by a cam 310 driven by motors (not shown). The cam 310 is eccentric to raise and lower the common point 308 and thereby raise and lower simultaneously the platform 67.

At the same time the platform 67 is connected to be moved laterally by a driven arm 312 which is actuated in turn by a thrust arm 314 which is tied to the cam 310 at the point 316 such that as the cam 310 rotates the point 316, being at an eccentric point on the cam 310. The platform 67 is moved laterally back and forth.

In operation the linear platform 67 is driven by the motion of the thrust arm 314 acting on the driven arm 312 to be moved first to the right in the drawing to move a distance sufficient to move the carriers 12 from one position to the next position. Thereafter the action of the cam 310 on the common point 308 is such as to allow the platform 67 to be lowered by the action of the springs so as to remove the pins 18 from the bottom of the carriers 12. This point is depicted by the dash line 18′ as described above. Next the platform 67 is moved to the left in the drawing as depicted by the arrow 75 so as to move the pins 18 from a forward position to the next rearward position of the carriers 12. Finally the carriers 12 again lifted as depicted by the arrow 69 and the pin motion 18′ to engage the carriers 12 of the next preceding position so that they too may be brought forward in the next cycle. The entire platform 67 is mounted to ride upon linear slides 300.

The several mixers 170 are driven by a belt 173 operated by a motor 172 driving pulleys 126. A single belt is used to drive the mixers 170 at the second, fourth and sixth positions in the incubation cycle. All of the first six processing positions are housed within a thermal housing 59. In addition, mixers 220 located at processing positions 8 and 9 (denoted by 193) are also driven by a belt 161 operated by a motor 160. A final mixer 192 is located also at position 10. It is operated by a drive motor 162 and belt 164. The thermal housing 59 only encloses operating positions 1 through 7 as noted. A first translating unit 20 is a robotic system of conventional design and operates a probe with two degrees of freedom namely in the X and Z directions. The first translator 20 has a probe, which operates as will be described in FIG. 12, to transfer sample from cup 280 (FIG. 9) into the reaction vessel 100 and reagent from the outer concentric portion 102 of the reaction vessel 100 to the reaction vessel 100 itself. In this connection, recall that the reaction vessel 100 is housed within a reaction vessel holder 90 which has the configuration described and is adapted to be nutated at its lower end.

At the wash positions 8 and 9, a wash means comprises a translating unit 410 (FIG. 7) having a single Z motion direction and is adapted to drive a probe 400 having concentric channels 404 in order to aspirate the fluid from the reaction vessel 100 and introduce clean wash liquid. The needles are connected to a peristaltic pump 168 (FIG. 12) through suitable tubing coaxial tubing 408. The translating mechanism designated by the numeral 410 is of a conventional type. At each wash position, a permanent magnet 412 which may be constructed of neodemium is attached to a lever arm 414 which is actuated at a pivot point 416 by a pulley drive 418. The pulley 422 is driven through a pulley belt 420 by a D.C. gear motor 421 to translate the magnet 412 near the reaction vessel holder 90 and then remove the magnet 412 from the reaction vessel holder 90 as depicted by the dashed line drawing 424. This, as will be described, operates to attract the magnetic particles to the side of the reaction vessel so that the aspiration will not remove the magnetic carrier particles.

At the final or tenth processing position there is a second translating unit 32 of the same conventional design as those described heretofore and having two degrees of movement in the X and Z directions. This translator 32 is positioned at an angle such that processed sample fluid may be withdrawn from the reaction vessel 100 and moved over and injected into the fluid container 272 through its rubber septum 268.

A third transport 34 means seen most clearly in FIG. 3 which is identical to and operates in the opposite sense to the first transport means 16 described previously. It too has folding pins (not shown) that operate to permit a pair of pins to be slid under the carrier 12 in that position, engage the receptacles 520 in the carrier 12 and then lock by being in the upright position to move the carrier 12 from the processing chamber 19 to the inlet chamber 10. Once this has occurred, the movement of the transport means 34 is reversed and the folding pins permitted to disengage from the bottom of the carrier 12 and move back to engage another carrier 12 in the processing chamber 19.

Figure 12:
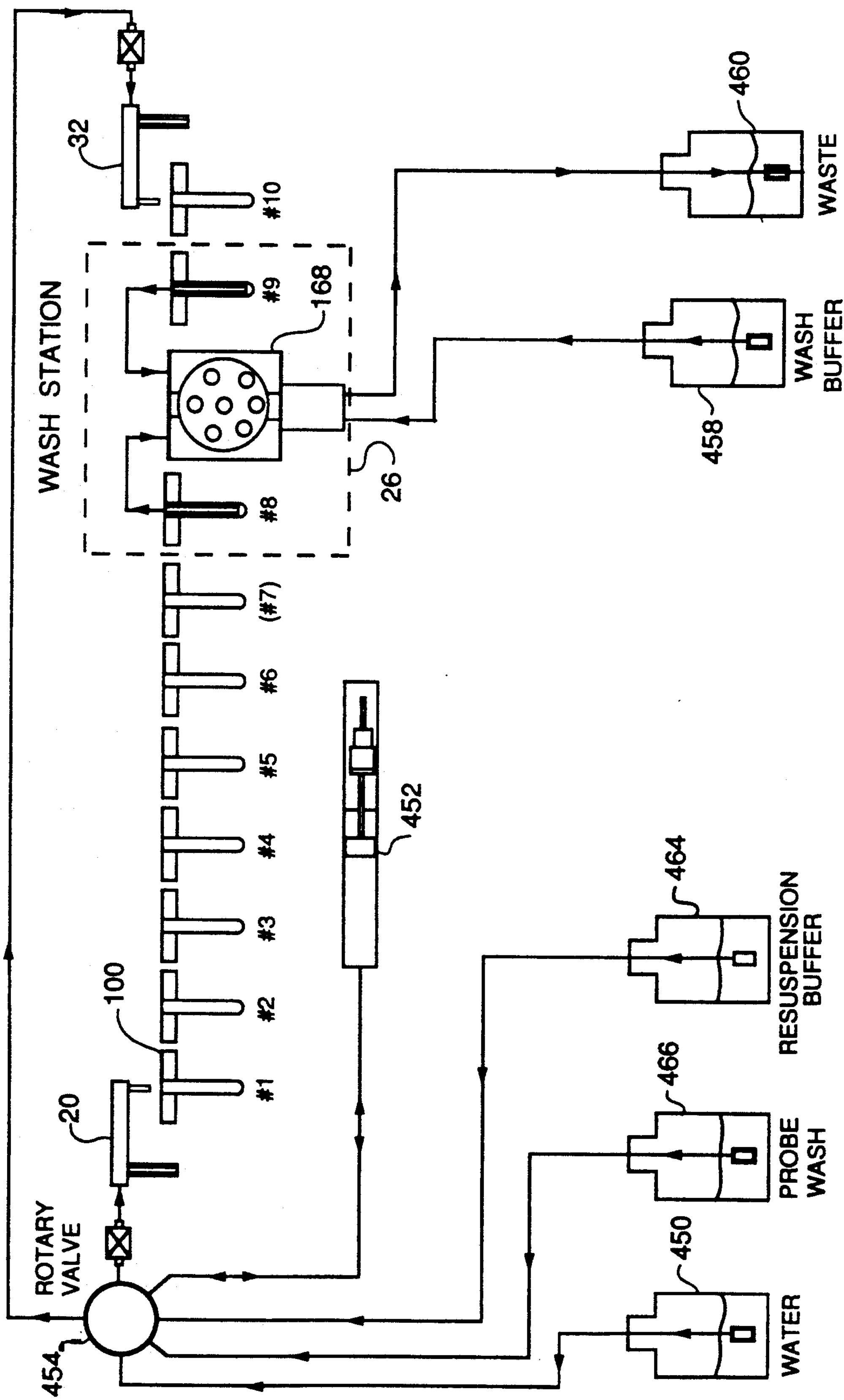
FIG. 12 is a liquid flow diagram depicting the liquid flows taking place during sample processing in the reaction vessel.

Finally a fifth transport means 36 (FIG. 8) operates to move the carriers 12 containing the completed sample reaction mixture into the exit area from which the process sample may be removed and transferred to an instrument for reading the results of the reaction. The liquid flow system is depicted in FIG. 12. This system depicts how the various liquids are applied to the reaction vessel 100 at the several positions to the 1, 8, 9 and 10 in the processing chamber 19. The first position is not shown. It is recalled that in this position sample and reagent and water each separated by an air bubble are withdrawn from the carrier 12 and water supply 450 and applied to the reaction vessel 100 at the first position. After this reaction vessel 100 are processed through the processing chamber 19.

The liquids are processed by using a syringe type pump 452 (FIG. 12) which is motor driven and actuated by the process controller 500 (FIG. 3). A peristaltic pump 168 is (1) to withdraw fluid from the wash buffer 458 and (2) provided to supply waste fluid to a waste disposal 460. The syringe type pump 452 operating through a rotary valve 454 supplies fluid from the resuspension buffer supply 464, a source of water 450, and the probe wash supply 466 for supply to the translators 20 and 32.

In operation, after having received the sample reagent and water at the first processing position the reaction mixture is allowed to incubate at positions 2 through 6. It is as previously described, vortexed position 2, 4 and 6. Following incubation, the next two units 8 and 9 are in the wash chamber 26. In this chamber 26, the magnets 412 are applied to the side of the reaction vessel 100 as previously described to cause the magnetic particles to clump at the sides. This allows the contents of the reaction vessels 100 at both positions 8 and 9 to initially have the liquid withdrawn therefrom and passed to the waste bottle 460. Thereafter fresh wash buffer is introduced from 458.

After passing through the wash station, the carrier 12 arrives at position 10. At this position the reaction vessel 100 is allowed to arrive virtually dry so that suspension buffer 464 may be added to the reaction vessel 100. The probe is washed thereafter with a suitable wash solution from the supply 466 such as sodium hypochloride plus sodium hydroxide. The mixer 192 at this position disperses the magnetic particles in the buffer. After this, the resuspended buffer is drawn up into the translator 32. The translator is repositioned and the withdrawn contents of the reaction vessel 100 inserted into the container 269. Following this action the carrier is moved back into the inlet chamber 10.

Figure 8:
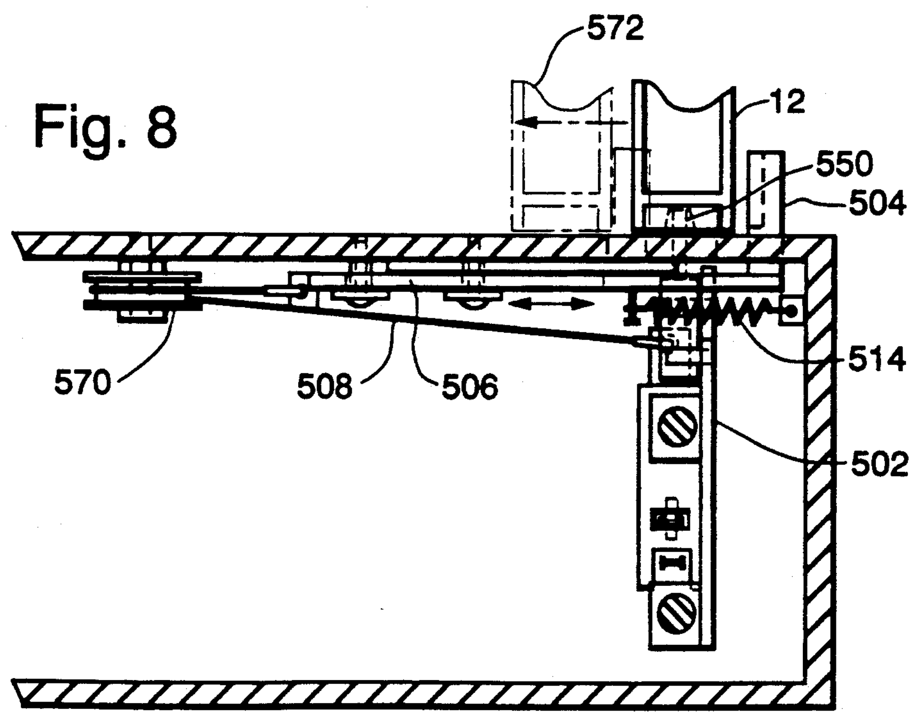
FIG. 8 is a view taken along the section line 8—8 of FIG. 3 to depict the mechanism which propels the carrier.

The mechanism for bringing this back to the inlet chamber 10 is used substantially the same as the transport mechanism which brought the carrier 12 from the inlet chamber 10 to the processing chamber 19 except that it operates in reverse as described. This is seen partially in FIG. 8. As depicted in FIG. 8, the carrier 12 is driven by the pin 550 from the carrier transport 502 into the inlet chamber 10. At this point the carrier 12 reverses and returns to the processing chamber. The carrier transport 502 is mounted on a slider mechanism 506 and is actuated by a wire 508 wrapped around a pulley 510. The other end of the wire 508 is attached to the carrier drive 502 such that as it returns to the processing chamber the wire 508 is tightened causing the lever arm 504 to be drawn against the carrier 12 shifting it to the position 512 illustrated by the dashed line. A spring 514 is attached to the slider arm 506 to return it and the lever 504 back to a withdrawn position when the carrier drive transport 502 again returns to the inlet area 10.

The apparatus utilizes a single time-template for processing the immunochemistry. The operations performed on each assay follows a fixed sequence and is governed by a fixed timing cycle. The operation sequence begins at position #1 (FIG. 1) where the patient sample, reagent and magnetic particles are mixed together to initiate the assay. Positions #2 through #7 are the incubation stations. Assays passing through these stations would received 6 cycles worth of incubation at the set temperature of 37° C. As the assays proceed to position #8 and #9, the dual wash stations would provide a total of three washes. The consumables are left "dry" as they advance into the exit station at position #10. At position #10, the captured analytes on the magnetic particles are resuspended and then injected into the aca® pack in the carrier.

Because the assays are to be run in an assembly line style, the stations are separated by their tasks and are programmed to function independently. A set of flowcharts are provided in FIG. 13A-13G to illustrate the processing structure of the instrument. These flowcharts are the basis of programming the CPU.

Description of Flow Charts

Figure 13A:
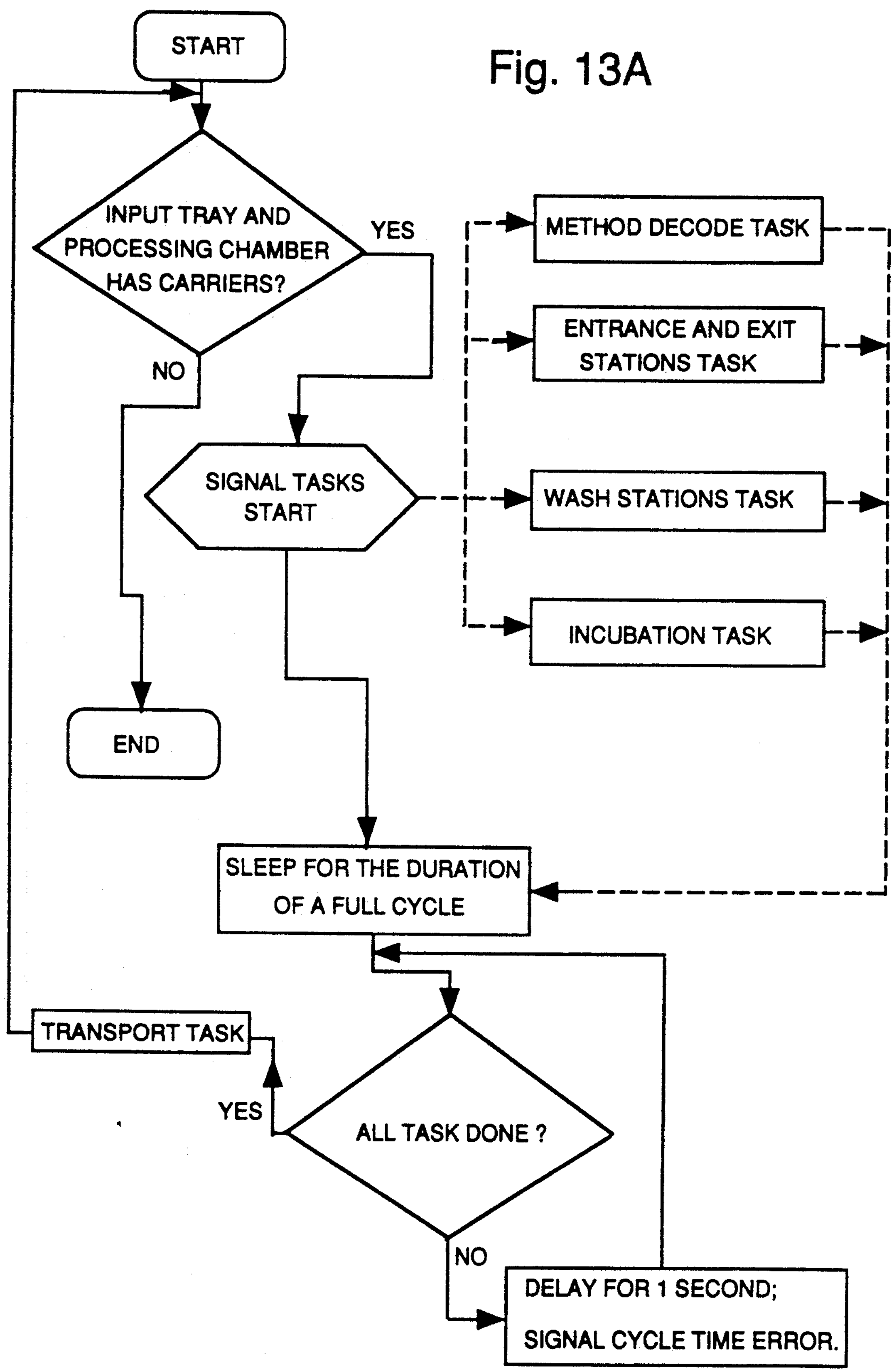
FIGS. 13 through 13 are flow charts of the software used to operate the apparatus of this invention.

FIG. 13A gives the overview of processing. The five tasks shown: method. decode task, entrance and exit stations task, wash stations task, incubation task and the transport task are initiated upon startup. Once started up, these tasks are expected to run as independent entities. Along with initiating the tasks, a method processing queue and task status flags are required in memory.

At the start of the processing loop in FIG. 13A, the input tray area 10 and the processing chamber (positions #1-#10) are checked as to whether carriers containing tests are in the instrument. The input tray has sensors (not shown) to detect carriers 12 waiting for processing. Once the carriers 12 begin their cycle in the processing chamber, the method processing queue keeps track of their locations. If any carrier is pending for processing or is undergoing processing, the four tasks: method decode, entrance and exit stations, wash stations and incubation, should check whether any carrier location are in their domain for processing. If there is, then the task should raise a busy status, proceed with processing, and clear their status flag when done. Once all the tasks are given the signal to begin, the processing loop would delay for the duration of one full cycle time. This operation is shown on FIG. 13A. The dotted line indicates the signal flow between the main processing loop to the different tasks. After the full cycle delay, the loop would continue by checking the status flag of each task. If all tasks are done, then the transport task is initiated to advance the carriers to their next position and the carrier locations are updated in the method processing queue. (FIG. 13G) However, if there are any busy tasks, then the system would raise a cycle time error and delay for a second prior to rechecking the status of all the tasks. After advancing the carriers to their next positions, the main processing loop would start again from the beginning until all carriers are processed.

Figure 13B:
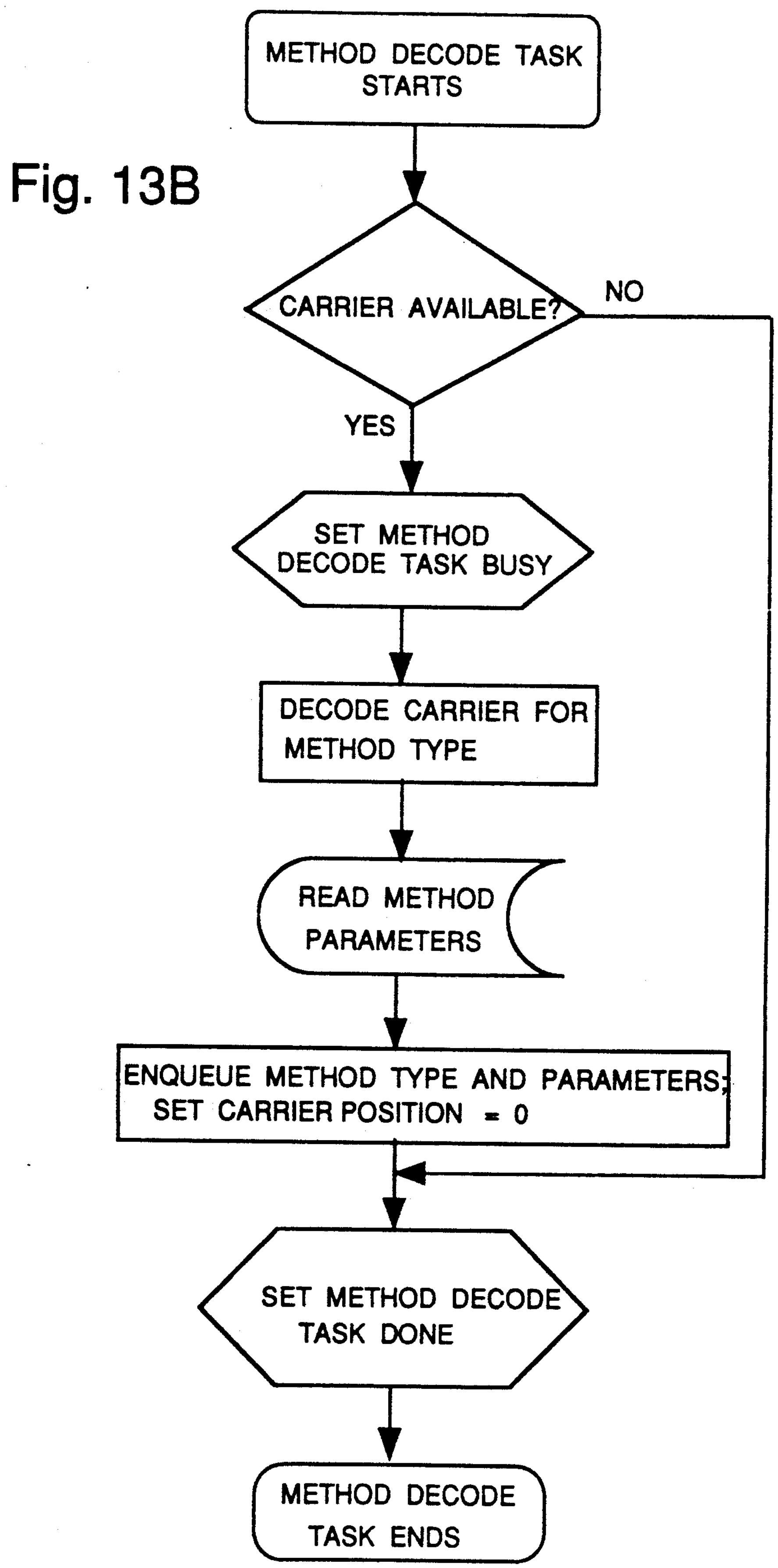

FIG. 13B gives the flowchart for the method decode task. If there is a carrier pending in the input tray, the method decode task would raise its busy flag. The aca ® pack 78 is decoded to determine which method type that carrier 12 contains. From the method type, the system would obtain from memory storage, the method specific parameters. This information is placed into the method processing queue and the carrier position for that test is set to 0. At this point, the carrier 12 would wait for the rectilinear transport (FIG. 5) to advance the carrier locations in the method processing queue and the entrance task to shuttle it into processing chamber 18. The method decode task's busy status is reset. And the method decode task ends.

FIGS. 13C and D gives the flowchart for the entrance and exit stations. Since the entrance and exit station shares the same precision fluid delivery pump, they require timing coordination to avoid conflicts in resource usage. Because of this, the processing cycle is further subdivided into two halves. The first half of the cycle is allotted to the exit station processing; while the second half belongs to the entrance station. When this task receives the start signal, it would check the method processing queue for the presence of a carrier 12. If any carrier location in the queue=1, then the carrier 12 in decode area 14 would be shuttled into position #1 where a possible preheating unit would bring the reaction vessel to approach the incubation chamber temperature.

In case the exit station may not finish processing in the allotted half cycle time, an entrance standby flag, set and reset by the exit station, is monitored after the entrance station delay to insure against any resource conflicts. After the delay to the 2nd half of the cycle and the standby flag indicating the pump resource is free, the entrance arm would proceed to aspirate the method specific volume of fluid from the aca ® sample cup on the carrier, aspirate the method specific volume of reagent from the consumable collar well and dispense both into the reaction vessel center well. The entrance arm needle is washed at this point. The entrance station busy flag is reset. While station #1 is running, if a carrier exists at position #10, the exit station would raise its busy flag and set the entrance station standby flag as well (FIG. 13D). This standby flag would give the entrance station an indication that the pump resource is busy. After the flags are set, the exit station needle would deliver a method specific volume of resuspension buffer into the center well of the reaction vessel. The mixer (FIG. 6) would spin up in one direction to resuspend the magnetic particles. The mixer would then be retracted by spinning in the opposite direction. The exit station needle would pick up a method specific amount of magnetic suspension and dispense it along with a method specific volume of resuspension buffer chase into the aca ® pack 269. The instrument would then wash the needle. After the needle washing routine is completed, the entrance standby flag may be reset to 0. This would allow the entrance station to begin its processing. At this point, the carrier 12 is free to be shuttled out of the processing chamber 18. Once the carrier 12 is out, the exit station task is completed. If both the entrance and exit station's status flag indicated that they are done, then the entrance/exit task is completed and should exit.

FIG. 13E shows the flowchart of the dual wash stations at position #8 and #9. When the wash station task receives the start signal from the main processing loop, it checks the method processing queue whether position #8 or #9 is filled. If a carrier 12 is in either station, then the wash station task raises a busy flag. Each wash station is required to go through two aspirate-dispense cycles in order to provide three complete clean washes. So the first operation is to set a loop variable to 1. The magnets are then moved against the consumable to begin the magnetic particle separation process. After waiting a number of seconds to allow the magnetic field to pull the magnetic particles into a pellet against the reaction vessel wall, the wash station task starts the peristaltic pump to pull out the "dirty" fluid. The valves for the aspirate lines at position #8 and #9 are opened and the wash probes are moved into the consumables. After allowing several seconds for the pump to suck the consumables dry, station #8 and #9 are checked for presence of an assay so as to determine which dispense lines may be opened along with the aspirate lines to allow rinsing of the probe. For station #9, it has an extra requirement that it should be the first wash loop before the dispense line would open. This is because the reaction vessels need to come out of the second wash station dry so that a resuspension buffer can be added at the exit station, position #10. After the dispense lines(s) are opened for a set amount of rinsing time, the aspirate line valves are closed. The dispense line(s) would remain open to dispense the specified amount of new wash buffer. Then the dispense valve(s) are closed, the pump is stopped, and the magnets and probes are withdrawn. The wash stations mixers are spun to its up position to resuspend magnetic particles in the new wash buffer. The mixers are then spun in the opposite direction to retract them. This completes the loop. The loop counter is incremented. The wash sequence is started again for the second aspirate-dispense cycle. After the second cycle is completed, the wash station task is done and it should exit.

Figure 13F:
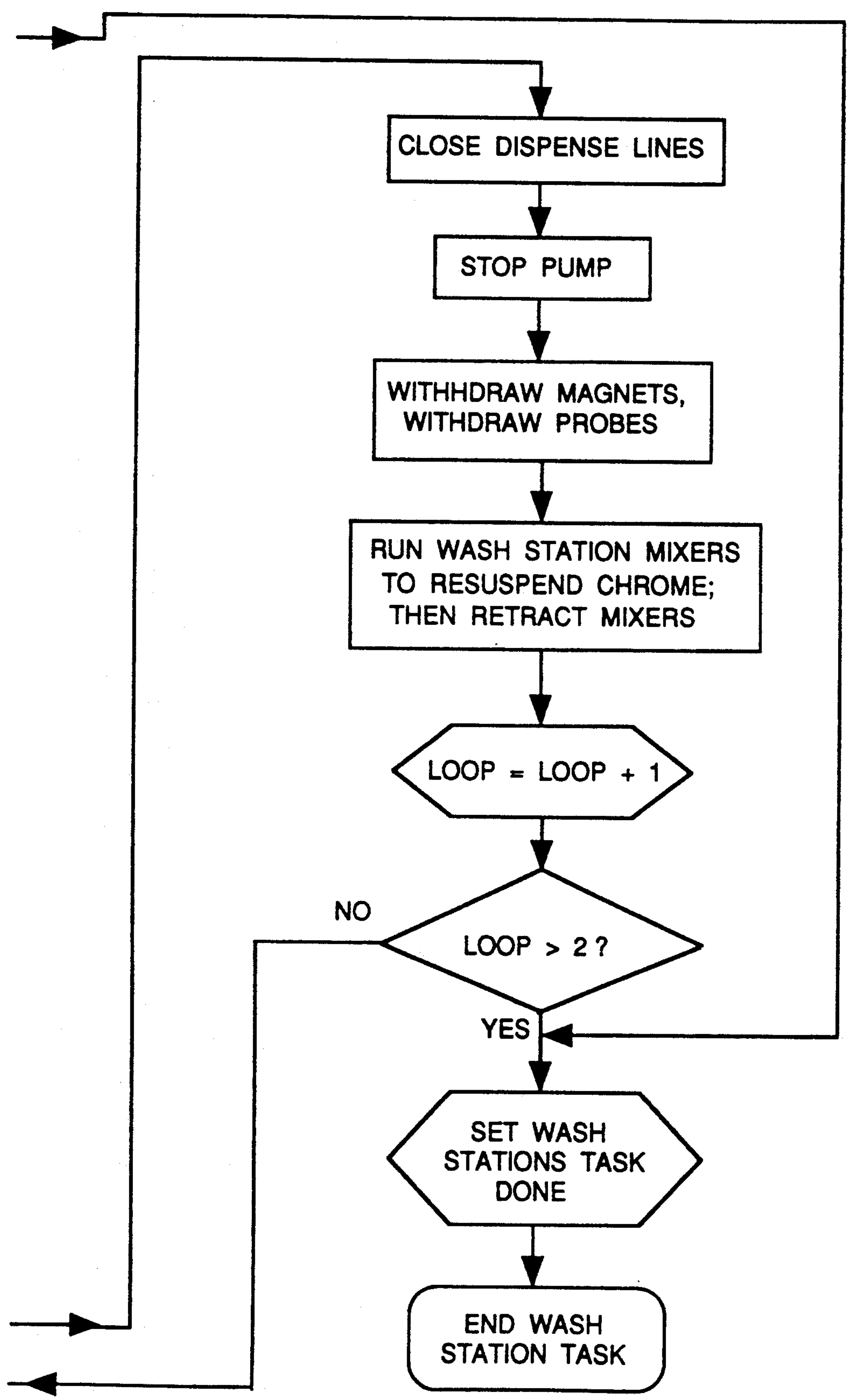
Figure 13G:
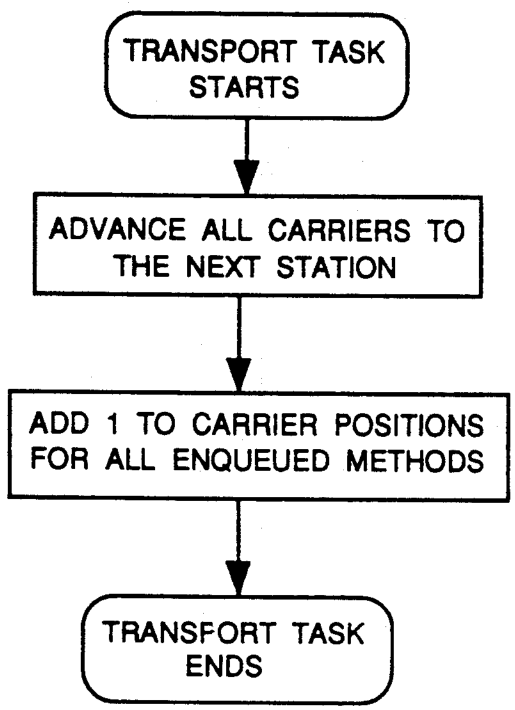
Figure 13H:
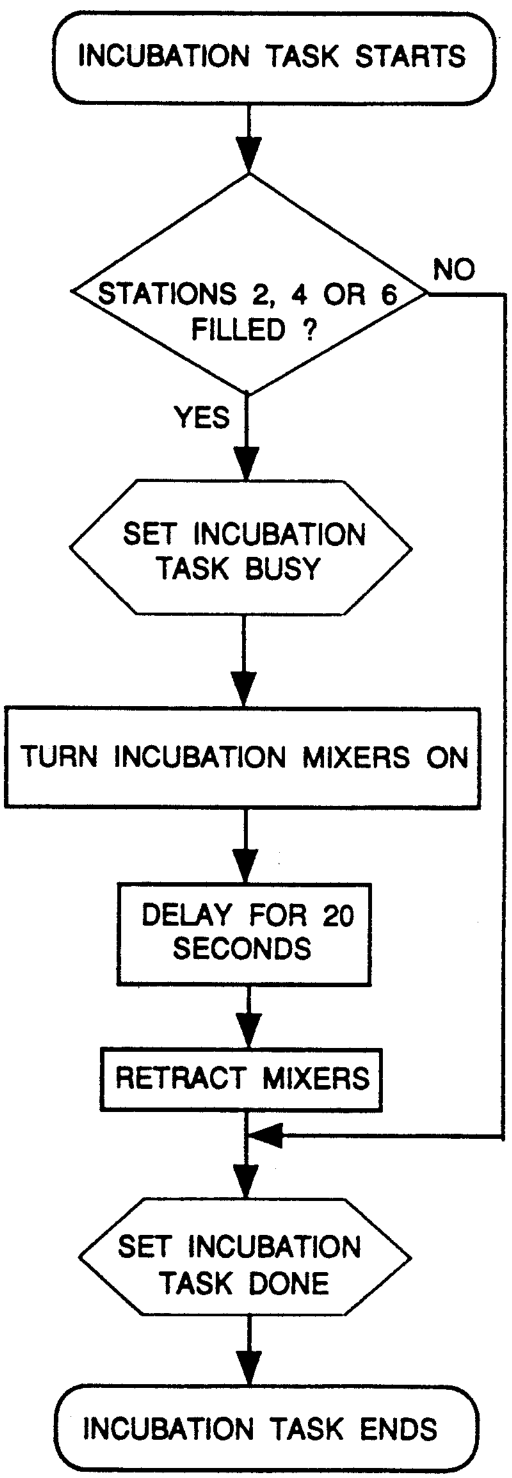

FIG. 13F shows the flowchart of the incubation task. Upon receiving the start signal from the main processing loop, it checks the method processing queue for carriers in positions #2, #4, and #6. If a carrier is in any of those positions, the incubation stations busy flag is set, and the incubation mixer spins for 20 seconds to keep the chrome particles dispersed in the sample and conjugate reagent mixture. At position #2, this mixing is also required to aid the dissolution of any tablets in the consumable center well. After 20 seconds, the mixers would spin in the opposite direction to retract them back to the down positions. Since the incubation temperature is controlled by electronic hardware, the incubation task does not have to be concerned about temperature control. At this point, the incubation task may reset the busy flag and should exit.

We claim:

1. An automatic multilinear apparatus for processing immunoassays of samples using a solid support, the assays having bound and free phases, the bound phase being bound to the solid support, the apparatus comprising:

an inlet chamber, a plurality of carriers positioned in the inlet chamber, each carrier holding a sample, a rotatably mounted reaction vessel, particles responsive to a magnetic field, reagents, and a reaction product container, a processing chamber generally parallel to the inlet chamber and having one end and the other end, first means to transport the plurality of carriers linearly in a first direction to one end of the inlet chamber, second means to transport sequentially the plurality of carriers linearly in a second direction transverse to the first direction from the one end of the inlet chamber to one end of the processing chamber, first translating means for acting on each carrier at the one end of the processing chamber to transfer each carrier's sample and reagents into the carrier's rotatably mounted reaction vessel, third means to transport sequentially the plurality of carriers linearly in a third direction opposite to and generally parallel to the first direction to several processing positions, means for vortexing at at least one processing position by nutating the lower portion of each rotatably mounted reaction vessel, wash means at at least one processing position for removing liquids from each rotatably mounted reaction vessel and replacing the liquids with a different liquid, magnet means at each wash means position for applying a magnetic field to each rotatably mounted reaction vessel prior to liquid removal, second translating means at the other end of the chamber processing for transferring the contents of each reaction vessel to its reaction product container, fourth means to transport each carrier transversely of the third direction from the processing chamber to the other end of the inlet chamber, and fifth means to transport each carrier from the other end of the inlet chamber in a direction generally parallel to the first direction for storage.

2. The apparatus of claim 1 wherein each carrier provided with at least a pair of receptacles positioned at the bottom of the carrier, and the second means has a pair of spring loaded pins foldable downwardly in the second direction, whereby the second means can be displaced in a direction opposite the second direction to engage each pair of receptacles and transport each carrier in the second direction.

3. The apparatus of claim 2 wherein the carrier defines a mounting orifice lined by a flexible material, the reaction vessel top portion being positioned in the orifice so that the lower end is nutatable.

4. The apparatus of claim 3 further comprising a thermal chamber capable of substantially enclosing the processing positions.

5. The apparatus of claim 4 wherein the third means includes pairs of fixed pins capable of engaging each of the plural carrier receptacles, and rectilinear transport means for raising each of the pair of fixed pins to engage the receptacles and displace the carrier's one processing position, and lowering each the pair of fixed pins to disengage the receptacles.

6. The apparatus of claim 5 wherein the magnet means includes a magnet, and means to displace the magnet to engage the side of the rotatably mounted reaction vessel, thereby to apply the magnetic field to the particles.

7. The apparatus of claim 6 wherein the fourth means has a pair of spring loaded pins foldable downwardly in the third direction, whereby the second means can be displaced in a direction opposite the third direction to engage each pair of carrier's receptacle to transport such carrier.

8. The apparatus of claim 7 wherein each carrier is provided with at least a pair of receptacles positioned at the bottom of the carrier, and the second means has a pair of spring loaded pins foldable downwardly in the second direction, whereby the second means can be displaced in a direction opposite the second direction to engage each pair of receptacles and transport each carrier in the second direction.

9. The apparatus of claim 7 further comprising a thermal chamber capable of substantially enclosing the processing positions.

10. The apparatus of claim 7 wherein the third means includes pairs of fixed pins capable of engaging each of the plural carrier receptacles, and rectilinear transport means for raising each of the pairs of fixed pins to engage the receptacles and displace the carriers one processing position, and lowering each pair of fixed pins to disengage the receptacles.

11. The apparatus of claim 2 further comprising a thermal chamber capable of substantially enclosing the processing positions.

12. The apparatus of claim 11 wherein the third means includes pairs of fixed pins capable of engaging each of the plural carrier receptacles, and rectilinear transport means for raising each of the pairs of fixed pins to engage the receptacles and displace the carriers one processing position, and lowering each pair of fixed pins to disengage the receptacles.

13. The apparatus of claim 1 wherein the carrier defines a mounting orifice lined by a flexible material, the reaction vessel top portion being positioned in the orifice so that the lower end is nutatable.

14. The apparatus of claim 1 which also includes a thermal chamber capable of substantially enclosing the processing positions.

15. The apparatus of claim 14 wherein each carrier is provided with at least a pair of receptacles positioned at the bottom of the carrier, and the second means has a pair of spring loaded pins foldable downwardly in the second direction, whereby the second means can be displaced in a direction opposite the second direction to engage each pair of receptacles and transport each carrier in the second direction.

16. The apparatus of claim 1 wherein the third means includes pairs of fixed pins capable of engaging each of the plural carrier receptacles, and rectilinear transport means for raising each of the pairs of fixed pins to engage the receptacles and-displace the carriers one processing position, and lowering each pair of fixed pins to disengage the receptacles.

17. The apparatus of claim 16 further comprising a thermal chamber capable of substantially enclosing the processing positions.

18. The apparatus of claim 17 wherein the magnet means includes a magnet, and means to displace the magnet to engage the side of the rotatably mounted reaction vessel, thereby to apply the magnetic field to the particles.

19. The apparatus of claim 1 wherein the magnet means includes a magnet, and means to displace the magnet to engage the side of the rotatably mounted reaction vessel, thereby to apply the magnetic field to the particles.

20. The apparatus of claim 19 wherein the third means includes pairs of fixed pins capable of engaging each of the plural carrier receptacles, and rectilinear transport means for raising each of the pairs of fixed pins to engage the receptacles and displace the carriers one processing position, and lowering each pair of fixed pins to disengage the receptacles.

21. The apparatus of claim 20 wherein each carrier is provided with at least a pair of receptacles positioned at the bottom of the carrier, and the second means has a pair of spring loaded pins foldable downwardly in the second direction, whereby the second means can be displaced in a direction opposite the second direction to engage each pair of receptacles and transport each carrier in the second direction.

* * * * *